US007220415B1

(12) United States Patent
Stalhammar-Carlemalm et al.

(10) Patent No.: US 7,220,415 B1
(45) Date of Patent: May 22, 2007

(54) VACCINE COMPOSITION

(75) Inventors: Margaretha Stalhammar-Carlemalm, Lund (SE); Thomas Areschoug, Lund (SE); Charlotte Larsson, Lund (SE); Gunnar Lindahl, Lund (SE)

(73) Assignee: Gunnar Lindahl, Lund (SE)

( * ) Notice: Subject to any disclaimer, the term of this patent is extended or adjusted under 35 U.S.C. 154(b) by 0 days.

(21) Appl. No.: 09/959,594

(22) PCT Filed: May 5, 2000

(86) PCT No.: PCT/IB00/00726

§ 371 (c)(1),
(2), (4) Date: May 21, 2002

(87) PCT Pub. No.: WO00/68259

PCT Pub. Date: Nov. 16, 2000

(30) Foreign Application Priority Data

May 5, 2001 (GB) ................................. 9910375.6

(51) Int. Cl.
  A61K 39/02 (2006.01)
  A61K 39/09 (2006.01)
  C12N 15/09 (2006.01)
  C07K 14/00 (2006.01)
  C07H 21/04 (2006.01)
(52) U.S. Cl. ................ 424/190.1; 424/197.1; 424/237.1; 424/244.1; 435/23.7; 530/350; 536/23.7
(58) Field of Classification Search ............. 424/237.1, 424/244.1, 190.1, 197.1; 435/69.1, 69.3, 435/253.4; 536/23.7; 530/350
See application file for complete search history.

(56) References Cited

U.S. PATENT DOCUMENTS 6,015,889 A * 1/2000 Lindahl et al. ............. 536/23.5
6,586,580 B1 * 7/2003 Lindahl et al. ............. 536/23.5

FOREIGN PATENT DOCUMENTS

| EP | 0 200 909 | 12/1986 |
| EP | 0 367 890 | 5/1990 |
| WO | WO 89/07649 | 8/1989 |
| WO | WO 94 10317 | 5/1994 |
| WO | WO 94/21685 | 9/1994 |
| WO | WO 98 06428 | 2/1998 |

OTHER PUBLICATIONS

Fenderson et al ; J. Immunol., Apr. 1989; 142: 2475-2481.*
Clinical Microbiological Reviews 2000, 13, 470-511.*
Rudinger et al, in "Peptide Hormones", edited by Parsons, J.A., University Park Press, Jun. 1976, p. 6.*
Burgess et al., The Journal of Cell Biology, 111:2129-2138, 1990.*
Lazar et al., Molecular and Cellular Biology, 8(3): 1247-1252, 1988.*
Jobling et al. (Mol. Microbiol. 1991, 5(7): 1755-67.*
1999, Mol.Microbio, 33(1) 208).*
Johnson 1975 (Infect Immun. 1975 Oct; 12(4): 901-9).*
Michel et al 1992, Database PIR_78, Acession No. 46405. Proc Natl Acad Sci U S A. Nov. 1, 1992;89(21): 10060-4.*
Wastefelt et al 1996, Database GenEmbl, Acession No. SAU 58333 (for nucleic acid sequence), Database SPTREMBL, Accession No. Q9XDB6 (for amino acid sequence). J.B.C. 1996, 271(3), 18892-18897.*
Clinical Microbiological Reviews 1998, 11; 497-513.*
Chappell et al, "Demonstration of protection in mice from a lethal challenge of three M serotypes of Streptococcus pyrogens using an M-negative vaccine", Vaccine, GB, Butterworth Scientific, Guildford, vol. 11, 1993, pp. 643-649.
Wäsfelt, "Identification of a family of streptococcal surface proteins with extremely repetitive structure", Journal of Biological Chemistry, vol. 271, No. 31, 1996, pp. 18892-18897.
Stalhammar-Carlemalm et al, "The R28 protein of Streptococcus pyrogens is related to several Group B streptococcal surface proteins, confers protective immunity and promotes binding to human epithelial cells" Molecular Microbiology, vol. 33, No. 1, Jul. 1999, pp. 208-219.
Stalhammar-Carlemalm et al, "Cross-protection between group A and group B Streptococci due to cross-reacting surface proteins", Journal of Infectious Diseases, vol. 182, No. 1, Jul. 2000, pp. 142-149.
Lachenauer et al, "Mosaicism in the alpha-like protein genes of group B Streptococci" Proceedings of the National Academy of Sciences of the United States, vol. 97, No. 17, Aug. 15, 2000, pp. 9630-9635.
Stanley et al, "molecular Subtyping of Prevalent M Serotypes of Streptococcus pyrogenes Causing Invasive Disease", Journal of Clinical Microbiology, Nov. 1995, pp. 2850-2855.
Larsson et al, "Experimental Vaccination against Group B Streptococcus, an Encapsulated Bacterium, with Highly Purified Preparations of Cell Surface Proteins Rib and α", Infection and Immunity, Sep. 1996, pp. 3518-3523.
Lancefield et al. "Preparation and properties of a protein (R antigen) occurring in Streptococci of group A, type 28 and in certain Streptococci of other serological groups" J. Exp. Med. 96:83-97 (1952).
Michel et al. "Large, identical, tandem repeating units in the C protein alpha antigen gene, bca, of group B Streptococci" Proc. Natl. Acad. Sci. USA 89:10060-10064 (1992).

* cited by examiner

Primary Examiner—Bruce R. Campell
Assistant Examiner—Padma Baskar
(74) Attorney, Agent, or Firm—Nixon & Vanderhye P.C.

(57) ABSTRACT

A polypeptide is described herein which comprises (a) the sequence of SEQ ID No. 2, (b) a variant of (a) which is capable of generating a protective immune response to S. pyogenes, or (c) a fragment of (a) or (b) of at least 6 amino acids in length which is capable of generating a protective immune response to S. pyogenes, in the manufacture of medicament for use as a vaccine against S. pyogenes. A pharmaceutical composition for use in vaccinating against S. pyogenes or Group B streptococcus comprises a polypeptide which comprises: (A) the amino acid sequence of SEQ ID No. 2, (B) a variant of (A) which is capable of conferring protective immunity to S. pyogenes or Group B streptococcus, or (C) a fragment of (A) or (B) of at least 6 amino acids in length which is capable of conferring protective immunity to S. pyogenes or Group B streptococcus.

11 Claims, 7 Drawing Sheets

FIG. 1A

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 3783 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION:1..3783

(xi) SEQUENCE DESCRIPTION: SEQ ID NO: 1:

```
ATG TTT AGA AGG TCT AAA AAT AAC AGT TAT GAT ACT TCA CAG ACG AAA      48
Met Phe Arg Arg Ser Lys Asn Asn Ser Tyr Asp Thr Ser Gln Thr Lys
 1               5                  10                  15

CAA CGG TTT TCA ATT AAG AAG TTC AAG TTT GGT GCA GCT TCT GTA CTA      96
Gln Arg Phe Ser Ile Lys Lys Phe Lys Phe Gly Ala Ala Ser Val Leu
                20                  25                  30

ATT GGT CTT AGT TTT TTG GGT GGG GTT ACA CAA GGT AAT CTT AAT ATT     144
Ile Gly Leu Ser Phe Leu Gly Gly Val Thr Gln Gly Asn Leu Asn Ile
            35                  40                  45

TTT GAA GAG TCA ATA GTT GCT GCA TCT ACA ATT CCA GGG AGT GCA GCG     192
Phe Glu Glu Ser Ile Val Ala Ala Ser Thr Ile Pro Gly Ser Ala Ala
        50                  55                  60

ACC TTA AAT ACA AGC ATC ACT AAA AAT ATA CAA AAC GGA AAT GCT TAC     240
Thr Leu Asn Thr Ser Ile Thr Lys Asn Ile Gln Asn Gly Asn Ala Tyr
65                  70                  75                  80

ATA GAT TTA TAT GAT GTA AAG AAT GGA TTG ATT GAT CCT CAA AAC CTC     288
Ile Asp Leu Tyr Asp Val Lys Asn Gly Leu Ile Asp Pro Gln Asn Leu
                85                  90                  95

ATT GTA TTA AAT CCA TCA AGC TAT TCA GCA AAT TAT TAT ATC AAA CAA     336
Ile Val Leu Asn Pro Ser Ser Tyr Ser Ala Asn Tyr Tyr Ile Lys Gln
                100                 105                 110

GGT GCT AAA TAT TAT AGT AAT CCG ATT GAA ATT ACA ACA ACT GGT TCA     384
```

```
                Gly Ala Lys Tyr Tyr Ser Asn Pro Ile Glu Ile Thr Thr Thr Gly Ser
                            115                 120                 125

GCA ACT ATT ACT TTT AAT ATA CTT GAT GAA ACT GGA AAT CCA CAT AAA                    432
Ala Thr Ile Thr Phe Asn Ile Leu Asp Glu Thr Gly Asn Pro His Lys
130                 135                 140

AAA GCT GAT GGA CAA ATT GAT ATA GTT AGT GTG AAT TTA ACT ATA TAT                    480
Lys Ala Asp Gly Gln Ile Asp Ile Val Ser Val Asn Leu Thr Ile Tyr
145                 150                 155                 160

GAT TCT ACA GCT TTA AGA AAT AGG ATA GAT GAA GTA ATA AAT AAT GCA                    528
Asp Ser Thr Ala Leu Arg Asn Arg Ile Asp Glu Val Ile Asn Asn Ala
                165                 170                 175

AAT GAT CCT AAG TGG AGT GAT GGG AGT CGT GAT GAA GTC TTA ACT GGA                    576
Asn Asp Pro Lys Trp Ser Asp Gly Ser Arg Asp Glu Val Leu Thr Gly
            180                 185                 190

TTA GAA AAA ATA AAA AAA GAT ATT GAT AAT AAT CCA AAA ACA CAA ATA                    624
Leu Glu Lys Ile Lys Lys Asp Ile Asp Asn Asn Pro Lys Thr Gln Ile
        195                 200                 205

GAT ATT GAT AAT AAA ATT AAT GAA GTC AAT GAA ATA GGG AAA TTG TTA                    672
Asp Ile Asp Asn Lys Ile Asn Glu Val Asn Glu Ile Gly Lys Leu Leu
    210                 215                 220

GTT GTA TCG CTA CCA GAT AAA ATT AAG TAT TCG CCA GAG GCT AAG CAT                    720
Val Val Ser Leu Pro Asp Lys Ile Lys Tyr Ser Pro Glu Ala Lys His
225                 230                 235                 240

AGG ACT GTT GAA CAA CAC GCG GAA TTA GAT GCA AAA GAT AGC ATT GCA                    768
Arg Thr Val Glu Gln His Ala Glu Leu Asp Ala Lys Asp Ser Ile Ala
                245                 250                 255

AAT ACA GAT GAA TTG CCA TCA AAT TCA ACG TAT AAC TGG AAA AAT GGT                    816
Asn Thr Asp Glu Leu Pro Ser Asn Ser Thr Tyr Asn Trp Lys Asn Gly
            260                 265                 270

CAT AAA CCA GAC ACC TCA ACA TCA GGT GAA AAA GAC GGA ATT GTT GAA                    864
His Lys Pro Asp Thr Ser Thr Ser Gly Glu Lys Asp Gly Ile Val Glu
        275                 280                 285

GTT CAC TAT CCA GAT GGT ACT GTT GAT GAT GTG AAT GTT AAA GTA ACC                    912
Val His Tyr Pro Asp Gly Thr Val Asp Asp Val Asn Val Lys Val Thr
    290                 295                 300

GTT ACA TCG AAA AAA ACT GAT AAT ACA GCT CCA ACA TTA ACC GTC ACT                    960
Val Thr Ser Lys Lys Thr Asp Asn Thr Ala Pro Thr Leu Thr Val Thr
305                 310                 315                 320

CCA GAG CAA CAG ACT GTT AAA GTG GAT GAA GAT ATT ACC TTT ACG GTT                   1008
Pro Glu Gln Gln Thr Val Lys Val Asp Glu Asp Ile Thr Phe Thr Val
                325                 330                 335

ACA GTT GAA GAC GAA AAT GAA GTT GAA CTA GGT TTA GAT GAT CTT AAA                   1056
Thr Val Glu Asp Glu Asn Glu Val Glu Leu Gly Leu Asp Asp Leu Lys
            340                 345                 350

GCT AAG TAT GAA AAT GAT ATC ATT GGA GCT CGT GTT AAA ATT AAG TAT                   1104
Ala Lys Tyr Glu Asn Asp Ile Ile Gly Ala Arg Val Lys Ile Lys Tyr
        355                 360                 365

CTT ACT AAA GAA CCT AAT AAG AAA GTC ATG GAA GTG ACA ATT ATG AAA                   1152
Leu Thr Lys Glu Pro Asn Lys Lys Val Met Glu Val Thr Ile Met Lys
    370                 375                 380

GCT ACT TTA GCA GAT AAG GGC GCA ATT ACC TTT ACT GCA AAA GAT AAA                   1200
Ala Thr Leu Ala Asp Lys Gly Ala Ile Thr Phe Thr Ala Lys Asp Lys
385                 390                 395                 400

GCA GGT AAT CAA GCA GAA CCT AAG ACA GTT ACC ATC AAT GTT CTT CCG                   1248
Ala Gly Asn Gln Ala Glu Pro Lys Thr Val Thr Ile Asn Val Leu Pro
                405                 410                 415

CTT AAG GAT AGC AAC GAA CCA AAA GGT AAG GAC CAA ACG GTC AAA GTA                   1296
Leu Lys Asp Ser Asn Glu Pro Lys Gly Lys Asp Gln Thr Val Lys Val
            420                 425                 430
```

```
                                            -continued

GGA GAA ACA CCG AAG GCA GAA GAT TCT ATT GGT AAC TTA TCA GAT CTT      1344
Gly Glu Thr Pro Lys Ala Glu Asp Ser Ile Gly Asn Leu Ser Asp Leu
            435                 440                 445

CCG AAA GGT ACA ACA GTA GCC TTT GAA GCT CCA GTT GAT ACA GCA ACA      1392
Pro Lys Gly Thr Thr Val Ala Phe Glu Ala Pro Val Asp Thr Ala Thr
        450                 455                 460

CCG GGA GAC AAA CCA GCA AAA GTT GTT GTG ACT TAC CCA GAT GGT TCA      1440
Pro Gly Asp Lys Pro Ala Lys Val Val Val Thr Tyr Pro Asp Gly Ser
465                 470                 475                 480

AAA GAT ACT GTA GAT GTG ACG GTT AAG GTT GTC GAT CCA CGT ACA GAT      1488
Lys Asp Thr Val Asp Val Thr Val Lys Val Val Asp Pro Arg Thr Asp
                485                 490                 495

GCC GAT AAG AAT GAT CCA GCA GGT AAG GAC CAA ACG GTC AAA GTA GGA      1536
Ala Asp Lys Asn Asp Pro Ala Gly Lys Asp Gln Thr Val Lys Val Gly
            500                 505                 510

GAA ACA CCG AAG GCA GAA GAT TCT ATT GGT AAC TTA TCA GAT CTT CCG      1584
Glu Thr Pro Lys Ala Glu Asp Ser Ile Gly Asn Leu Ser Asp Leu Pro
        515                 520                 525

AAA GGT ACA ACA GTA GCC TTT GAA GCT CCA GTT GAT ACA GCA ACA CCG      1632
Lys Gly Thr Thr Val Ala Phe Glu Ala Pro Val Asp Thr Ala Thr Pro
    530                 535                 540

GGA GAC AAA CCA GCA AAA GTT GTT GTG ACT TAC CCA GAT GGT TCA AAA      1680
Gly Asp Lys Pro Ala Lys Val Val Val Thr Tyr Pro Asp Gly Ser Lys
545                 550                 555                 560

GAT ACT GTA GAT GTG ACG GTT AAG GTT GTC GAT CCA CGT ACA GAT GCC      1728
Asp Thr Val Asp Val Thr Val Lys Val Val Asp Pro Arg Thr Asp Ala
                565                 570                 575

GAT AAG AAT GAT CCA GCA GGT AAG GAC CAA ACG GTC AAA GTA GGA GAA      1776
Asp Lys Asn Asp Pro Ala Gly Lys Asp Gln Thr Val Lys Val Gly Glu
            580                 585                 590

ACA CCG AAG GCA GAA GAT TCT ATT GGT AAC TTA TCA GAT CTT CCG AAA      1824
Thr Pro Lys Ala Glu Asp Ser Ile Gly Asn Leu Ser Asp Leu Pro Lys
        595                 600                 605

GGT ACA ACA GTA GCC TTT GAA GCT CCA GTT GAT ACA GCA ACA CCG GGA      1872
Gly Thr Thr Val Ala Phe Glu Ala Pro Val Asp Thr Ala Thr Pro Gly
    610                 615                 620

GAC AAA CCA GCA AAA GTT GTT GTG ACT TAC CCA GAT GGT TCA AAA GAT      1920
Asp Lys Pro Ala Lys Val Val Val Thr Tyr Pro Asp Gly Ser Lys Asp
625                 630                 635                 640

ACT GTA GAT GTG ACG GTT AAG GTT GTC GAT CCA CGT ACA GAT GCC GAT      1968
Thr Val Asp Val Thr Val Lys Val Val Asp Pro Arg Thr Asp Ala Asp
                645                 650                 655

AAG AAT GAT CCA GCA GGT AAG GAC CAA ACG GTC AAA GTA GGA GAA ACA      2016
Lys Asn Asp Pro Ala Gly Lys Asp Gln Thr Val Lys Val Gly Glu Thr
            660                 665                 670

CCG AAG GCA GAA GAT TCT ATT GGT AAC TTA TCA GAT CTT CCG AAA GGT      2064
Pro Lys Ala Glu Asp Ser Ile Gly Asn Leu Ser Asp Leu Pro Lys Gly
        675                 680                 685

ACA ACA GTA GCC TTT GAA GCT CCA GTT GAT ACA GCA ACA CCG GGA GAC      2112
Thr Thr Val Ala Phe Glu Ala Pro Val Asp Thr Ala Thr Pro Gly Asp
    690                 695                 700

AAA CCA GCA AAA GTT GTT GTG ACT TAC CCA GAT GGT TCA AAA GAT ACT      2160
Lys Pro Ala Lys Val Val Val Thr Tyr Pro Asp Gly Ser Lys Asp Thr
705                 710                 715                 720

GTA GAT GTG ACG GTT AAG GTT GTC GAT CCA CGT ACA GAT GCC GAT AAG      2208
Val Asp Val Thr Val Lys Val Val Asp Pro Arg Thr Asp Ala Asp Lys
                725                 730                 735

AAT GAT CCA GCA GGT AAG GAC CAA ACG GTC AAA GTA GGA GAA ACA CCG      2256
Asn Asp Pro Ala Gly Lys Asp Gln Thr Val Lys Val Gly Glu Thr Pro
            740                 745                 750
```

```
                                                      -continued

AAG GCA GAA GAT TCT ATT GGT AAC TTA TCA GAT CTT CCG AAA GGT ACA     2304
Lys Ala Glu Asp Ser Ile Gly Asn Leu Ser Asp Leu Pro Lys Gly Thr
            755                 760                 765

ACA GTA GCC TTT GAA GCT CCA GTT GAT ACA GCA ACA CCG GGA GAC AAA     2352
Thr Val Ala Phe Glu Ala Pro Val Asp Thr Ala Thr Pro Gly Asp Lys
        770                 775                 780

CCA GCA AAA GTT GTT GTG ACT TAC CCA GAT GGT TCA AAA GAT ACT GTA     2400
Pro Ala Lys Val Val Val Thr Tyr Pro Asp Gly Ser Lys Asp Thr Val
785                 790                 795                 800

GAT GTG ACG GTT AAG GTT GTC GAT CCA CGT ACA GAT GCC GAT AAG AAT     2448
Asp Val Thr Val Lys Val Val Asp Pro Arg Thr Asp Ala Asp Lys Asn
                805                 810                 815

GAT CCA GCA GGT AAG GAC CAA ACG GTC AAA GTA GGA GAA ACA CCG AAG     2496
Asp Pro Ala Gly Lys Asp Gln Thr Val Lys Val Gly Glu Thr Pro Lys
            820                 825                 830

GCA GAA GAT TCT ATT GGT AAC TTA TCA GAT CTT CCG AAA GGT ACA ACA     2544
Ala Glu Asp Ser Ile Gly Asn Leu Ser Asp Leu Pro Lys Gly Thr Thr
        835                 840                 845

GTA GCC TTT GAA GCT CCA GTT GAT ACA GCA ACA CCG GGA GAC AAA CCA     2592
Val Ala Phe Glu Ala Pro Val Asp Thr Ala Thr Pro Gly Asp Lys Pro
850                 855                 860

GCA AAA GTT GTT GTG ACT TAC CCA GAT GGT TCA AAA GAT ACT GTA GAT     2640
Ala Lys Val Val Val Thr Tyr Pro Asp Gly Ser Lys Asp Thr Val Asp
865                 870                 875                 880

GTG ACG GTT AAG GTT GTC GAT CCA CGT ACA GAT GCC GAT AAG AAT GAT     2688
Val Thr Val Lys Val Val Asp Pro Arg Thr Asp Ala Asp Lys Asn Asp
            885                 890                 895

CCA GCA GGT AAG GAC CAA ACG GTC AAA GTA GGA GAA ACA CCG AAG GCA     2736
Pro Ala Gly Lys Asp Gln Thr Val Lys Val Gly Glu Thr Pro Lys Ala
        900                 905                 910

GAA GAT TCT ATT GGT AAC TTA TCA GAT CTT CCG AAA GGT ACA ACA GTA     2784
Glu Asp Ser Ile Gly Asn Leu Ser Asp Leu Pro Lys Gly Thr Thr Val
    915                 920                 925

GCC TTT GAA GCT CCA GTT GAT ACA GCA ACA CCG GGA GAC AAA CCA GCA     2832
Ala Phe Glu Ala Pro Val Asp Thr Ala Thr Pro Gly Asp Lys Pro Ala
930                 935                 940

AAA GTT GTT GTG ACT TAC CCA GAT GGT TCA AAA GAT ACT GTA GAT GTG     2880
Lys Val Val Val Thr Tyr Pro Asp Gly Ser Lys Asp Thr Val Asp Val
945                 950                 955                 960

ACG GTT AAG GTT GTC GAT CCA CGT ACA GAT GCC GAT AAG AAT GAT CCA     2928
Thr Val Lys Val Val Asp Pro Arg Thr Asp Ala Asp Lys Asn Asp Pro
            965                 970                 975

GCA GGT AAG GAC CAA ACG GTC AAA GTA GGA GAA ACA CCG AAG GCA GAA     2976
Ala Gly Lys Asp Gln Thr Val Lys Val Gly Glu Thr Pro Lys Ala Glu
        980                 985                 990

GAT TCT ATT GGT AAC TTA TCA GAT CTT CCG AAA GGT ACA ACA GTA GCC     3024
Asp Ser Ile Gly Asn Leu Ser Asp Leu Pro Lys Gly Thr Thr Val Ala
    995                 1000                1005

TTT GAA GCT CCA GTT GAT ACA GCA ACA CCG GGA GAC AAA CCA GCA AAA     3072
Phe Glu Ala Pro Val Asp Thr Ala Thr Pro Gly Asp Lys Pro Ala Lys
    1010                1015                1020

GTT GTT GTG ACT TAC CCA GAT GGT TCA AAA GAT ACT GTA GAT GTG ACG     3120
Val Val Val Thr Tyr Pro Asp Gly Ser Lys Asp Thr Val Asp Val Thr
1025                1030                1035                1040

GTT AAG GTT GTC GAT CCA CGT ACA GAT GCC GAT AAG AAT GAT CCA GCA     3168
Val Lys Val Val Asp Pro Arg Thr Asp Ala Asp Lys Asn Asp Pro Ala
            1045                1050                1055

GGT AAG GAC CAA ACG GTC AAA GTA GGA GAA ACA CCG AAG GCA GAA GAT     3216
Gly Lys Asp Gln Thr Val Lys Val Gly Glu Thr Pro Lys Ala Glu Asp
```

```
                1060               1065               1070
TCT ATT GGT AAC TTA TCA GAT CTT CCG AAA GGT ACA ACA GTA GCC TTT      3264
Ser Ile Gly Asn Leu Ser Asp Leu Pro Lys Gly Thr Thr Val Ala Phe
        1075               1080               1085

GAA GCT CCA GTT GAT ACA GCA ACA CCG GGA GAC AAA CCA GCA AAA GTT      3312
Glu Ala Pro Val Asp Thr Ala Thr Pro Gly Asp Lys Pro Ala Lys Val
    1090               1095               1100

GTT GTG ACT TAC CCA GAT GGT TCA AAA GAT ACT GTA GAT GTG ACG GTT      3360
Val Val Thr Tyr Pro Asp Gly Ser Lys Asp Thr Val Asp Val Thr Val
1105               1110               1115               1120

AAG GTT GTC GAT CCA CGT ACA GAT GCC GAT AAG AAT GAT CCA GCA GGT      3408
Lys Val Val Asp Pro Arg Thr Asp Ala Asp Lys Asn Asp Pro Ala Gly
                1125               1130               1135

AAG GAC CAA ACG GTC AAA GTA GGA GAA ACA CCG AAG GCA GAA GAT TCT      3456
Lys Asp Gln Thr Val Lys Val Gly Glu Thr Pro Lys Ala Glu Asp Ser
            1140               1145               1150

ATT GGT AAC TTA TCA GAT CTT CCG AAA GGT ACA ACA GTA GCC TTT GAA      3504
Ile Gly Asn Leu Ser Asp Leu Pro Lys Gly Thr Thr Val Ala Phe Glu
        1155               1160               1165

GCT CCA GTT GAT ACA GCA ACA CCG GGA GAC AAA CCA GCA AAA GTT GTT      3552
Ala Pro Val Asp Thr Ala Thr Pro Gly Asp Lys Pro Ala Lys Val Val
    1170               1175               1180

GTG ACT TAC CCA GAT GGT TCA AAA GAT ACT GTA GAT GTG ACG GTT AAG      3600
Val Thr Tyr Pro Asp Gly Ser Lys Asp Thr Val Asp Val Thr Val Lys
1185               1190               1195               1200

GTT GTC GAT CCA CGT ACA GAT GCC GAT AAG AAT GAT CCA GCA GGT AAA      3648
Val Val Asp Pro Arg Thr Asp Ala Asp Lys Asn Asp Pro Ala Gly Lys
                1205               1210               1215

AAT CAG CAA GTC AAA GGT AAA GGA AAT AAA CTA CCA GCA ACA GGT GAG      3696
Asn Gln Gln Val Lys Gly Lys Gly Asn Lys Leu Pro Ala Thr Gly Glu
            1220               1225               1230

AAT GCG ACT CCA TTC TTT AAT GTT GCA GCT TTG ACA ATT ATA TCA TCA      3744
Asn Ala Thr Pro Phe Phe Asn Val Ala Ala Leu Thr Ile Ile Ser Ser
        1235               1240               1245

GTT GGT TTA TTA TCT GTT TCT AAG AAA AAA GAG GAT TAA                  3783
Val Gly Leu Leu Ser Val Ser Lys Lys Lys Glu Asp
    1250               1255               1260

(2) INFORMATION FOR SEQ ID NO: 2:

(i) SEQUENCE CHARACTERISTICS:
        (A) LENGTH: 1260 amino acids
        (B) TYPE: amino acid
        (D) TOPOLOGY: linear (ii) MOLECULE TYPE: protein (xi) SEQUENCE DESCRIPTION: SEQ ID NO: 2:

Met Phe Arg Arg Ser Lys Asn Asn Ser Tyr Asp Thr Ser Gln Thr Lys
1               5                   10                  15

Gln Arg Phe Ser Ile Lys Lys Phe Lys Phe Gly Ala Ala Ser Val Leu
            20                  25                  30

Ile Gly Leu Ser Phe Leu Gly Gly Val Thr Gln Gly Asn Leu Asn Ile
        35                  40                  45

Phe Glu Glu Ser Ile Val Ala Ala Ser Thr Ile Pro Gly Ser Ala Ala
    50                  55                  60

Thr Leu Asn Thr Ser Ile Thr Lys Asn Ile Gln Asn Gly Asn Ala Tyr
65                  70                  75                  80

Ile Asp Leu Tyr Asp Val Lys Asn Gly Leu Ile Asp Pro Gln Asn Leu
            85                  90                  95
```

-continued

```
Ile Val Leu Asn Pro Ser Ser Tyr Ser Ala Asn Tyr Tyr Ile Lys Gln
            100                 105                 110

Gly Ala Lys Tyr Tyr Ser Asn Pro Ile Glu Ile Thr Thr Gly Ser
        115                 120                 125

Ala Thr Ile Thr Phe Asn Ile Leu Asp Glu Thr Gly Asn Pro His Lys
        130                 135                 140

Lys Ala Asp Gly Gln Ile Asp Ile Val Ser Val Asn Leu Thr Ile Tyr
145                 150                 155                 160

Asp Ser Thr Ala Leu Arg Asn Arg Ile Asp Glu Val Ile Asn Asn Ala
                165                 170                 175

Asn Asp Pro Lys Trp Ser Asp Gly Ser Arg Asp Glu Val Leu Thr Gly
            180                 185                 190

Leu Glu Lys Ile Lys Asp Ile Asp Asn Asn Pro Lys Thr Gln Ile
        195                 200                 205

Asp Ile Asp Asn Lys Ile Asn Glu Val Asn Glu Ile Gly Lys Leu Leu
210                 215                 220

Val Val Ser Leu Pro Asp Lys Ile Lys Tyr Ser Pro Glu Ala Lys His
225                 230                 235                 240

Arg Thr Val Glu Gln His Ala Glu Leu Asp Ala Lys Asp Ser Ile Ala
                245                 250                 255

Asn Thr Asp Glu Leu Pro Ser Asn Ser Thr Tyr Asn Trp Lys Asn Gly
            260                 265                 270

His Lys Pro Asp Thr Ser Thr Ser Gly Glu Lys Asp Gly Ile Val Glu
        275                 280                 285

Val His Tyr Pro Asp Gly Thr Val Asp Val Asn Val Lys Val Thr
    290                 295                 300

Val Thr Ser Lys Lys Thr Asp Asn Thr Ala Pro Thr Leu Thr Val Thr
305                 310                 315                 320

Pro Glu Gln Gln Thr Val Lys Val Asp Glu Asp Ile Thr Phe Thr Val
                325                 330                 335

Thr Val Glu Asp Glu Asn Glu Val Glu Leu Gly Leu Asp Asp Leu Lys
            340                 345                 350

Ala Lys Tyr Glu Asn Asp Ile Ile Gly Ala Arg Val Lys Ile Lys Tyr
        355                 360                 365

Leu Thr Lys Glu Pro Asn Lys Lys Val Met Glu Val Thr Ile Met Lys
    370                 375                 380

Ala Thr Leu Ala Asp Lys Gly Ala Ile Thr Phe Thr Ala Lys Asp Lys
385                 390                 395                 400

Ala Gly Asn Gln Ala Glu Pro Lys Thr Val Thr Ile Asn Val Leu Pro
                405                 410                 415

Leu Lys Asp Ser Asn Glu Pro Lys Gly Lys Asp Gln Thr Val Lys Val
            420                 425                 430

Gly Glu Thr Pro Lys Ala Glu Asp Ser Ile Gly Asn Leu Ser Asp Leu
        435                 440                 445

Pro Lys Gly Thr Thr Val Ala Phe Glu Ala Pro Val Asp Thr Ala Thr
    450                 455                 460

Pro Gly Asp Lys Pro Ala Lys Val Val Thr Tyr Pro Asp Gly Ser
465                 470                 475                 480

Lys Asp Thr Val Asp Val Thr Val Lys Val Asp Pro Arg Thr Asp
                485                 490                 495

Ala Asp Lys Asn Asp Pro Ala Gly Lys Asp Gln Thr Val Lys Val Gly
            500                 505                 510
```

-continued

```
Glu Thr Pro Lys Ala Glu Asp Ser Ile Gly Asn Leu Ser Asp Leu Pro
        515                 520                 525
Lys Gly Thr Thr Val Ala Phe Glu Ala Pro Val Asp Thr Ala Thr Pro
        530                 535                 540
Gly Asp Lys Pro Ala Lys Val Val Thr Tyr Pro Asp Gly Ser Lys
545                 550                 555                 560
Asp Thr Val Asp Val Thr Val Lys Val Val Asp Pro Arg Thr Asp Ala
                565                 570                 575
Asp Lys Asn Asp Pro Ala Gly Lys Asp Gln Thr Val Lys Val Gly Glu
            580                 585                 590
Thr Pro Lys Ala Glu Asp Ser Ile Gly Asn Leu Ser Asp Leu Pro Lys
        595                 600                 605
Gly Thr Thr Val Ala Phe Glu Ala Pro Val Asp Thr Ala Thr Pro Gly
        610                 615                 620
Asp Lys Pro Ala Lys Val Val Thr Tyr Pro Asp Gly Ser Lys Asp
625                 630                 635                 640
Thr Val Asp Val Thr Val Lys Val Val Asp Pro Arg Thr Asp Ala Asp
                645                 650                 655
Lys Asn Asp Pro Ala Gly Lys Asp Gln Thr Val Lys Val Gly Glu Thr
            660                 665                 670
Pro Lys Ala Glu Asp Ser Ile Gly Asn Leu Ser Asp Leu Pro Lys Gly
        675                 680                 685
Thr Thr Val Ala Phe Glu Ala Pro Val Asp Thr Ala Thr Pro Gly Asp
        690                 695                 700
Lys Pro Ala Lys Val Val Thr Tyr Pro Asp Gly Ser Lys Asp Thr
705                 710                 715                 720
Val Asp Val Thr Val Lys Val Val Asp Pro Arg Thr Asp Ala Asp Lys
                725                 730                 735
Asn Asp Pro Ala Gly Lys Asp Gln Thr Val Lys Val Gly Glu Thr Pro
            740                 745                 750
Lys Ala Glu Asp Ser Ile Gly Asn Leu Ser Asp Leu Pro Lys Gly Thr
        755                 760                 765
Thr Val Ala Phe Glu Ala Pro Val Asp Thr Ala Thr Pro Gly Asp Lys
        770                 775                 780
Pro Ala Lys Val Val Thr Tyr Pro Asp Gly Ser Lys Asp Thr Val
785                 790                 795                 800
Asp Val Thr Val Lys Val Val Asp Pro Arg Thr Asp Ala Asp Lys Asn
                805                 810                 815
Asp Pro Ala Gly Lys Asp Gln Thr Val Lys Val Gly Glu Thr Pro Lys
            820                 825                 830
Ala Glu Asp Ser Ile Gly Asn Leu Ser Asp Leu Pro Lys Gly Thr Thr
        835                 840                 845
Val Ala Phe Glu Ala Pro Val Asp Thr Ala Thr Pro Gly Asp Lys Pro
        850                 855                 860
Ala Lys Val Val Thr Tyr Pro Asp Gly Ser Lys Asp Thr Val Asp
865                 870                 875                 880
Val Thr Val Lys Val Val Asp Pro Arg Thr Asp Ala Asp Lys Asn Asp
                885                 890                 895
Pro Ala Gly Lys Asp Gln Thr Val Lys Val Gly Glu Thr Pro Lys Ala
            900                 905                 910
Glu Asp Ser Ile Gly Asn Leu Ser Asp Leu Pro Lys Gly Thr Thr Val
        915                 920                 925
Ala Phe Glu Ala Pro Val Asp Thr Ala Thr Pro Gly Asp Lys Pro Ala
```

```
                        930             935             940
Lys Val Val Thr Tyr Pro Asp Gly Ser Lys Asp Thr Val Asp Val
945                 950             955                 960

Thr Val Lys Val Val Asp Pro Arg Thr Asp Ala Asp Lys Asn Asp Pro
            965             970             975

Ala Gly Lys Asp Gln Thr Val Lys Val Gly Glu Thr Pro Lys Ala Glu
            980             985             990

Asp Ser Ile Gly Asn Leu Ser Asp Leu Pro Lys Gly Thr Thr Val Ala
            995             1000            1005

Phe Glu Ala Pro Val Asp Thr Ala Thr Pro Gly Asp Lys Pro Ala Lys
            1010            1015            1020

Val Val Val Thr Tyr Pro Asp Gly Ser Lys Asp Thr Val Asp Val Thr
1025            1030            1035            1040

Val Lys Val Val Asp Pro Arg Thr Asp Ala Asp Lys Asn Asp Pro Ala
            1045            1050            1055

Gly Lys Asp Gln Thr Val Lys Val Gly Glu Thr Pro Lys Ala Glu Asp
            1060            1065            1070

Ser Ile Gly Asn Leu Ser Asp Leu Pro Lys Gly Thr Thr Val Ala Phe
            1075            1080            1085

Glu Ala Pro Val Asp Thr Ala Thr Pro Gly Asp Lys Pro Ala Lys Val
            1090            1095            1100

Val Val Thr Tyr Pro Asp Gly Ser Lys Asp Thr Val Asp Val Thr Val
1105            1110            1115            1120

Lys Val Val Asp Pro Arg Thr Asp Ala Asp Lys Asn Asp Pro Ala Gly
            1125            1130            1135

Lys Asp Gln Thr Val Lys Val Gly Glu Thr Pro Lys Ala Glu Asp Ser
            1140            1145            1150

Ile Gly Asn Leu Ser Asp Leu Pro Lys Gly Thr Thr Val Ala Phe Glu
            1155            1160            1165

Ala Pro Val Asp Thr Ala Thr Pro Gly Asp Lys Pro Ala Lys Val Val
            1170            1175            1180

Val Thr Tyr Pro Asp Gly Ser Lys Asp Thr Val Asp Val Thr Val Lys
1185            1190            1195            1200

Val Val Asp Pro Arg Thr Asp Ala Asp Lys Asn Asp Pro Ala Gly Lys
            1205            1210            1215

Asn Gln Gln Val Lys Gly Lys Gly Asn Lys Leu Pro Ala Thr Gly Glu
            1220            1225            1230

Asn Ala Thr Pro Phe Phe Asn Val Ala Ala Leu Thr Ile Ile Ser Ser
            1235            1240            1245

Val Gly Leu Leu Ser Val Ser Lys Lys Lys Glu Asp
1250            1255            1260
```

(2) INFORMATION FOR SEQ ID NO: 3:

(i) SEQUENCE CHARACTERISTICS:
        (A) LENGTH: 79 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

```
Gly Lys Asp Gln Thr Val Lys Val Gly Glu Thr Pro Lys Ala Glu Asp
1               5               10              15

Ser Ile Gly Asn Leu Ser Asp Leu Pro Lys Gly Thr Thr Val Ala Phe
```

-continued

```
              20                  25                  30
Glu Ala Pro Val Asp Thr Ala Thr Pro Gly Asp Lys Pro Ala Lys Val
        35                  40                  45

Val Val Thr Tyr Pro Asp Gly Ser Lys Asp Thr Val Asp Val Thr Val
     50                  55                  60

Lys Val Val Asp Pro Arg Thr Asp Ala Asp Lys Asn Asp Pro Ala
 65                  70                  75
```

VACCINE COMPOSITION

This application is a national phase application of International Patent Appln. No. PCT/IB00/00726 filed May 5, 2000, which designated the U.S.

FIELD OF THE INVENTION

This invention relates to vaccine compositions comprising R28 protein of S. pyogenes or fragments thereof and polynucleotides encoding the polypeptide.

BACKGROUND OF THE INVENTION

Streptococcus pyogenes Group A streptococcus, is a common human pathogen that is best known as the cause of throat and skin infections. S. pyogenes also has the potential to cause more serious and potentially life threatening diseases such as scarlet fever and toxic shock like syndrome. S. pyogenes has also been implicated as the cause of the majority of cases of puerperal fever.

The surface antigen R28 is expressed by some strains of S. pyogenes. Early studies indicated that R28 is unrelated to virulence (Lancefield and Perlmann. J. Exp. Med (1952) 96:83–97), since antibodies to R28 did not protect mice against lethal infection with an R28-expressing strain of S. pyogenes.

Group B Streptococcus (GBS) is found in the normal flora of the human vagina and may cause life-threatening disease in newborn children who are often exposed to GBS at birth. Most isolates of GBS express either of the surface proteins Rib or a which are members of the same protein family.

SUMMARY OF THE INVENTION

The surface antigen R28 has now been characterised at the molecular level. The nucleotide sequence and amino acid sequence of R28 have been identified. In contrast to an earlier report (Lancefield and Perlmann 1952), the ability of antibodies to R28 to protect mice against lethal infection with an R28-expressing strain of S. pyogenes has been demonstrated. In addition, antibodies to R28 can protect mice against lethal infection with strains of group B streptococcus, and in particular, to GBS strains which express protein Rib or a Rib-like protein. Thus, R28 can elicit cross-protection against Rib-expressing strains of GBS, although the two proteins show only limited immunological cross-reactivity. Protein Rib antibodies can also protect mice against lethal infection with an R28-expressing strain of Group A streptococcus, S. pyogenes.

Since preparations of R28 elicit a protective immune response, they may be used in a vaccine composition to protect against R28-expressing strains of S. pyogenes. In addition, polypeptides which bind R28 antibodies may be used in a vaccine composition to protect against Rib and Rib-like expressing strains of group B streptococcus. Some of the vaccine compositions incorporating particular polypeptides derived from R28 are in themselves novel. Polynucleotides encoding such polypeptides are also novel and form part of the invention.

In a first aspect, the invention provides use of a polypeptide which comprises:

(a) the sequence of SEQ ID No:2,
(b) a variant of (a) which is capable of generating a protective immune response to S. pyogenes, or
(c) a fragment of (a) or (b) of at least 6 amino acids in length which is capable of generating a protective immune response to S. pyogenes, in the manufacture of a medicament for use as a vaccine against S. pyogenes.

In another aspect, the invention relates to novel polynucleotides having a sequence selected from:

(i) the DNA sequence of SEQ ID No: 1 or the sequence complementary thereto,
(ii) a sequence which selectively hybridises to a said sequence (i) or a fragment thereof, or
(iii) a sequence which codes for a polypeptide having the same amino acid sequence as that encoded by a said sequence (i) or (ii).

The invention also relates a recombinant vector, such as an expression vector, comprising a polynucleotide of the invention operably linked to a regulatory sequence, for example a promoter; a host cell which is transformed with a polynucleotide of the invention; and a process of producing a polypeptide suitable for use in vaccination against S. pyogenes or Group B Streptococcus comprising maintaining a host cell transformed with a polynucleotide of the invention under conditions to provide expression of the polypeptide.

In a further aspect, the invention provides a vaccine composition for use in vaccination against S. pyogenes or Group B Streptococcus, comprising a polypeptide encoded by a polynucleotide of the invention together with a pharmaceutically acceptable carrier. Preferably the polypeptide comprises:

(A) the amino acid sequence of SEQ ID NO: 2.
(B) a variant of (A) that is capable of generating protective immunity to S. pyogenes or Group B Streptococcus, or
(C) a fragment of (A) or (B) of at least 6 amino acids in length that is capable of conferring protective immunity to S. pyogenes or Group B Streptococcus.

In a further aspect, the invention provides a method of vaccinating a subject against S. pyogenes, comprising administering to said subject an effective amount of a polypeptide which comprises:

(a) the amino acid sequence of SEQ ID No 2.
(b) a variant of (a) which is capable of binding an anti-R28 antibody, or
(c) a fragment of (a) or (b) of at 6 least amino acids in length which is capable of binding an anti-R28 antibody.

In a further aspect, the invention provides a method of vaccinating a subject against S. pyogenes or Group B streptococcus comprising administering to said subject an effective amount of the polypeptide which comprises:

(A) the amino acid sequence of SEQ ID NO: 2,
(B) a variant of (A) that is capable of generating protective immunity to S. pyogenes or Group B Streptococcus, or
(C) a fragment of (A) or (B) of at least 6 amino acids in length that is capable of conferring protective immunity to S. pyogenes or Group B Streptococcus.

Overall structure of R28. Rib and α, and amino acid residue identity between different regions of the proteins. (C) Schematic representation of R28, indicating the position of subregions, defined on the basis of sequence similarities with GBS proteins α,β and Rib.

Figure 2:
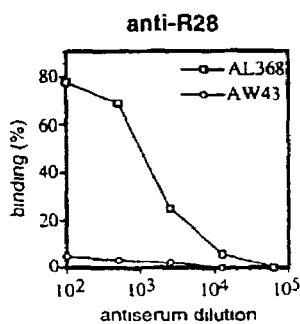

FIG. 2. Analysis of surface expression. Suspensions of R28 positive strain AL386 and R-28 negative strain AW43 were incubated with mouse anti-R28 serum. Bound antibodies were detected by the addition of radiolabeled protein A. Binding (%) refers to the fraction of added protein A.

FIG. 3. Characterization of an R28-negative *S. pyogenes* mutant and use of this mutant to analyze the role of R28 in adhesion to human cervical cells. (A) The mutant lacks surface expression of R28. (B) Binding of the R28 positive strain and its R28-negative mutant to the human cervical cell line ME180.

Figure 4B:
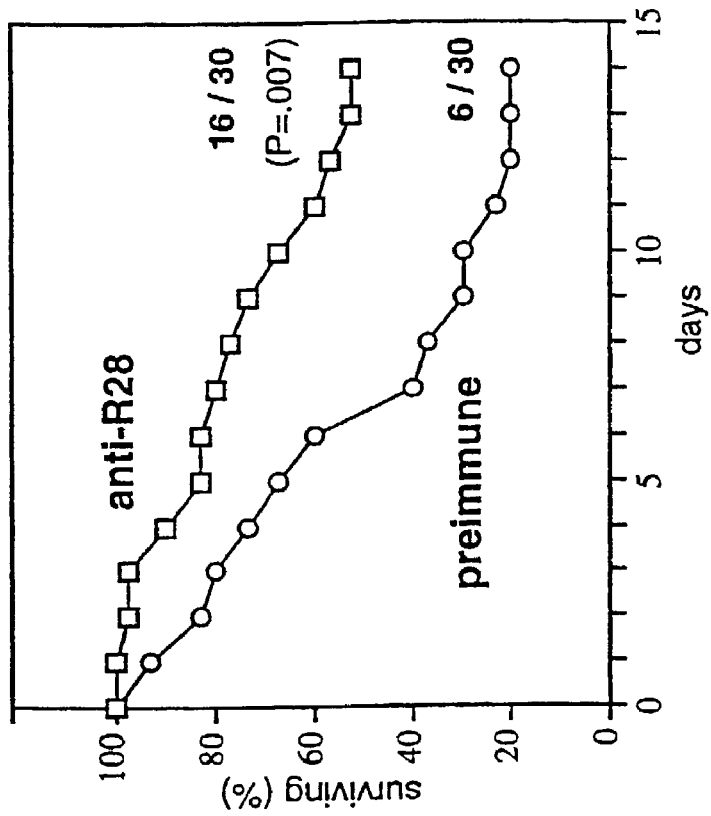
Figure 4A:
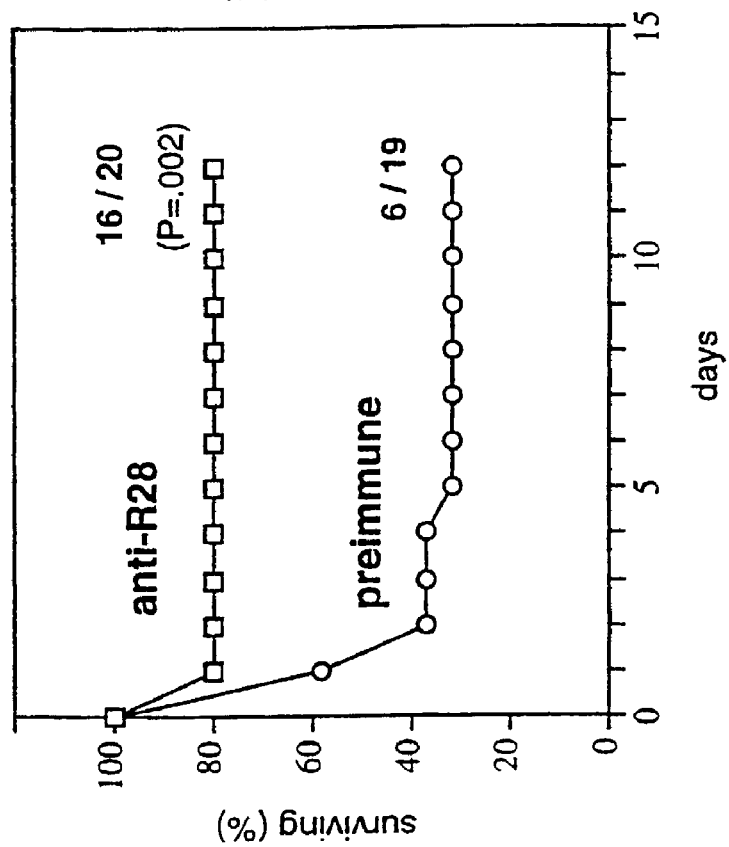

FIG. 4. Antibodies to R28 protect mice against lethal *S. pyogenes* infection. (A) shows the final ratios (number of surviving mice number of challenged mice) in a challenge with $4 \times 10^4$ cfu of the R28-expressing reference strain "Griffith Small". (B) As in panel A, but the mice were challenged with $3 \times 10^7$ cfu of the R28-expressing puerperal fever isolate 2369–97.

FIG. 5. Analysis of the immunological cross-reactivity between R28 and Rib. A: Inhibition tests with highly purified proteins. In the left panel, the binding of rabbit anti-R28 to immobilized R28 was inhibited by the addition of increasing amounts of R28, Rib or β, as indicated. In the right panel, the binding of anti-Rib to immobilized Rib was inhibited with the same proteins. B: Inhibition tests with whole bacteria. In the left panel, the binding of mouse anti-R28 to immobilized R28 was inhibited by the addition of increasing amounts of washed bacteria. Strains used were the R28-expressing GAS strain AL368, the rib-expressing GBS strain BM110, and the GAS strain AW43, which does not express R28 or Rib (control). In the right panel, the binding of mouse anti-Rib to Rib was inhibited with the same bacteria.

FIG. 6. Vaccination with purified R28 or Rib confers cross-protection. A: each of the six panels shows an experiment in which one group of mice was immunized with pure R28 and one group (control) was immunized with BSA. Immunized mice were challenged i.p. with an $\sim LD^{90}$ dose of the GBS strain indicated in the upper right-hand corner. For each of these GBS strains, the following information is given: relevant surface protein, capsular serotype, and name of the strain. Following challenge with the GBS strain, deaths were recorded daily for seven days. Differences in survival in the two groups were used to calculate P values. B: mice were immunized with pure Rib or with PBS (control), and challenged with the R28-expressing GAS strain "Griffith". Experiments performed as described under A. C: mice were immunized s.c. with living bacteria of the R28-expressing strain AL368 or with strain AW43, which does not express R28. The immunized mice were challenged with the Rib-expressing GBS stain BM110.

FIG. 7. Immunological comparison of R28 proteins expressed by different GAS isolates and of Rib (or Rib-like) proteins expressed by different GBS isolates. In each panel, the binding of mouse antibodies to an immobilized protein was inhibited by the addition of whole washed bacteria. A: binding of mouse anti-R28 to immobilized R28 was inhibited with different GAS strains. The figures shows data obtained with four representative R28-expressing strains and with one strain not expressing R28 (strain AW43). B: binding of mouse anti-Rib to immobilized Rib was inhibited with different GBS strains. The figure shows data obtained with four representative Rib-expressing strains of serotype III or II, and with one type Ib strain not expressing Rib. Strains used were BM110. BS30, 1954/92, 118/158 and SB35. C: binding of mouse anti-Rib to immobilized Rib was inhibited with the Rib-expressing strain BM110 (control) and with two GBS strains expressing proteins related to Rib or R28. The type V strain 2471 expresses a Rib-like protein. The type III strain D136C expresses a protein that crossreacts with R28 but not with Rib.

DESCRIPTION OF THE SEQUENCES

SEQ ID No.1 sets out the amino acid sequence for full length R28 of *S. pyogenes* strain AL368 and the gene encoding this protein named spr28. The first 56 amino acids of this sequence comprise a signal sequence. The mature protein commences with serine at position 57. The numbering used in SEQ ID No.1 is thus different from that used in FIG. 1A where the signal sequence is numbered beginning at −56 and the first serine of the mature protein is designated 1. The structure of R28 is discussed in more detail below.

SEQ ID No.2 is the amino acid sequence alone for full length R28.

Figure 1A:
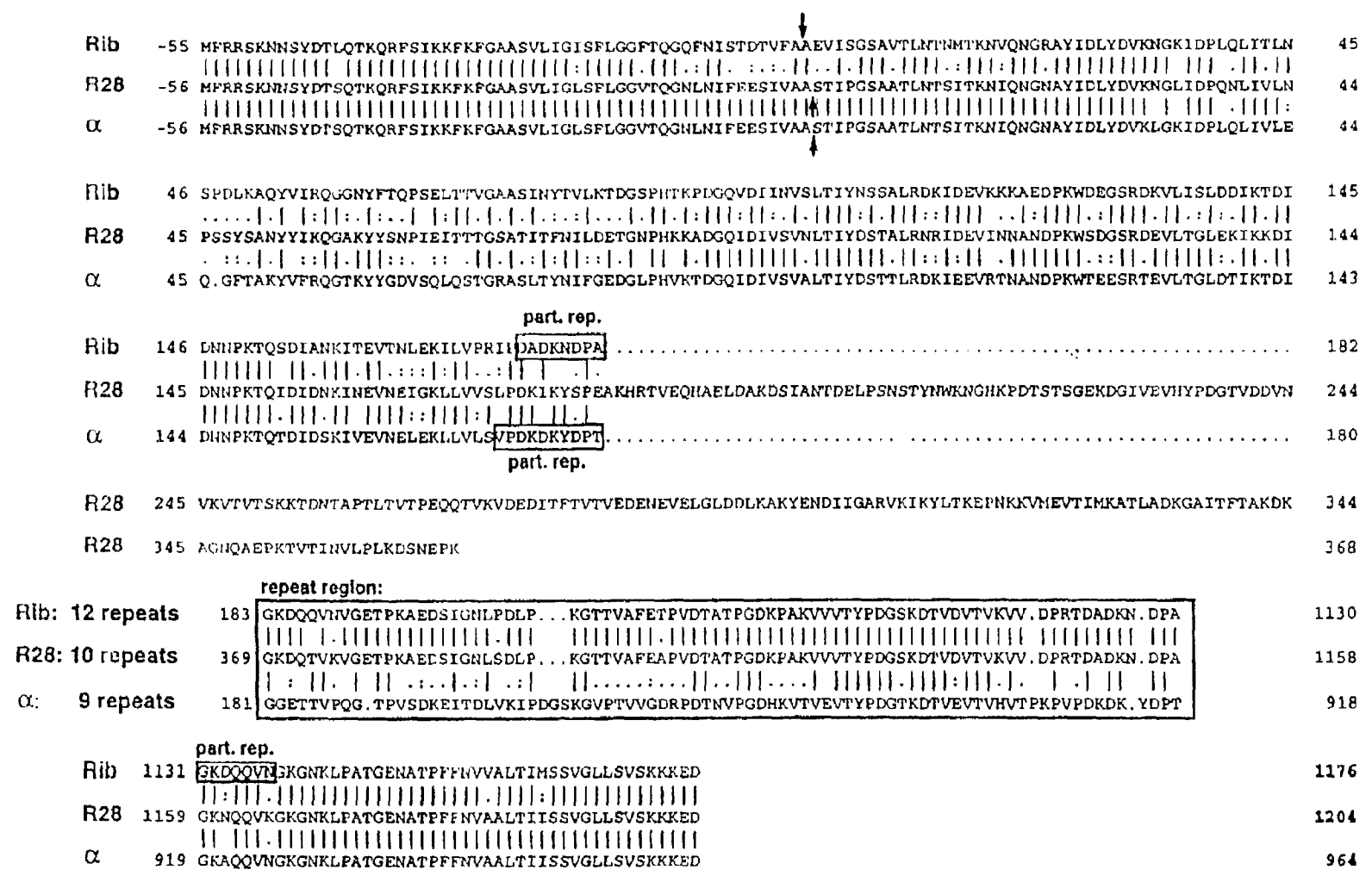

SEQ ID No.3 is the amino acid sequence of the region of residues 425–503 of SEQ ID No.2 (369–447 of FIG. 1A). This sequence is present as multiple repeats in protein R28.

DETAILED DESCRIPTION OF THE INVENTION

Use of Polypeptides in the Manufacture of Vaccine Compositions Against Group A *Streptococcus*

The invention provides the use of certain polypeptides in the manufacture of vaccine compositions which can be used to protect against infection with some strains of Group A *streptococcus, S. pyogenes*. In particular, the vaccine composition is useful to protect against infection with R28 expressing strains of *S. pyogenes*. References to *S. pyogenes* below may therefore read as preferably R28 expressing strains.

Polypeptides for use in accordance with this embodiment of the invention in particular are those polypeptides which are capable of binding an anti-R28 antibody. Such antibodies could be raised against purified antigen such as whole protein R28 as described in more detail in the Examples below. Antibodies can be monoclonal or polyclonal antibodies. Typically, the antibodies confer protective immunity to Group A *Streptococcus*. Polypeptides for use in the embodiment of the invention could also be described as those polypeptides which confer protective immunity to Group A *Streptococcus* following administration to a mammal.

Polypeptides for use in this embodiment of the invention may bind antibodies specific for R28 with the proviso that some such antibodies may also demonstrate cross-reactivity with protein Rib of Group B Streptococcus. GBS.

Polypeptides for use in the manufacture of vaccine compositions to confer protective immunity to Group A *Streptococcus* may comprise (a) the sequence SEQ ID NO. 2.

(b) a variant of SEQ ID NO. 2; or (c) a fragment of at least 6 amino acids in length of the sequence of (a) or (b). In each case, the polypeptide is capable of conferring protective immunity to Group A *Streptococcus*.

Antisera to polypeptides of the invention can be generated by standard techniques, for example, by injection of the polypeptide into an appropriate animal and collection and purification of antisera from animals. Antibodies which bind R28 or a variant or fragments thereof in accordance with the invention can be identified by standard immunoassays. Antibodies so obtained can then be injected into mice in a lethal challenge with R28 expressing *S. pyogenes* strains as set out in more detail in the examples below. The antibodies so obtained may also be used to isolate or purify polypeptides for incorporation into the vaccine compositions of the invention.

Polypeptides can be administered directly to mammals. Subsequently, mammals such as mice can be subjected to a lethal challenge with R28 expressing *S. pyogenes* strains to establish whether the prior vaccination with polypeptide has conferred protective immunity on the mammal.

A polypeptide for use in the invention consists essentially of the amino acid sequence set out in SEQ ID NO: 2 or a variant thereof or of a fragment of either of the sequences.

A variant for incorporation in the vaccine composition against *S. pyogenes* is one which will confer protective immunity to *S. pyogenes*. Preferably, such polypeptides will react with anti-R28 antibodies. Over the entire length of SEQ ID NO; 2, a variant will preferably be at least 70% homologous to that sequence based on amino acid identity. Polypeptides to be incorporated into an *S. pyogenes* vaccine composition may comprise a fragment of SEQ ID No 2. Preferably, such fragments comprise a polypeptide having the sequence of part or all of the repeat SEQ ID No 3. Preferably, a variant comprises a sequence that is at least 90% homologous (identical) to SEQ ID NO: 3.

It will be appreciated that protein Rib of Group B *Streptococcus* falls within the definition of variants set out above for incorporation in a vaccine composition against *S. pyogenes*. As has been demonstrated below, protein Rib can confer protective immunity to Group A *Streptococcus*. Fragments of protein Rib may also be incorporated into a vaccine composition for immunising against *S. pyogenes*. Thus the vaccine composition for use in vaccination against *S. pyogenes* may comprise protein Rib, or a variant sequence thereof, or a fragment of either sequence which is capable of generating a protective immune response to *S. pyogenes*. All references to variations in SEQ ID NO. 2 for use in a vaccine composition against Group A *Streptococcus* should be read as also referring to possible variations in protein Rib, such variations providing polypeptides which maintain the ability to provide protective immunity to Group A *Streptococcus*.

Amino acid substitutions may be made to SEQ ID NO: 2 or 3, for example, from 1, 2 or 3 up to 10, 20 or 30 substitutions. The modified polypeptide retains the ability to generate an immune response and confer protective immunity to R28-expressing *S. pyogenes*. Conservative substitutions may be made, for example, according to the following table 1. Amino acids in the same block in the second column and preferably in the same line in the third column may be substituted for each other:

TABLE 1

| ALIPHATIC | Non-polar | G A P |
| --- | --- | --- |
| | | I L V |
| | Polar - uncharged | C S T M |
| | | N Q |
| | Polar - charged | D E |
| | | K R |
| AROMATIC | | H F W Y |

One or more amino acid residues of SEQ ID No 2 or 3 may alternatively or additionally be deleted. From 1, 2 or 3 to 10, 20 or 30 residues may be deleted, or more. Polypeptides of the invention also include fragments of the above-mentioned sequences. Such fragments retain the ability to bind R28 antibodies and preferably will confer protective immunity to *S. pyogenes*. Fragments may be at least from 10, 12, 15 or 20 to 60, 100 or 200 amino acids in length. For SEQ ID No a fragment may be at least from 10, 12, 15 or 20 to 40, 50 or 60 amino acids in length.

Polypeptides for Incorporation in a Vaccine Composition According to the Invention In preferred embodiments, the invention relates to new vaccine compositions comprising preferred polypeptides of the invention. Such vaccine compositions are preferred embodiments for immunisation against *S. pyogenes* as described above. The preferred vaccine compositions of the invention may also be used to confer protective immunity to Group B *Streptococcus*.

Polypeptides for use in accordance for this aspect of the invention are those polypeptides which are capable of binding an anti-R28 antibody or of binding an anti-Rib antibody. Polypeptides for use in vaccine compositions against Group B *Streptococcus* in accordance with the invention do not encompass protein Rib or a fragment thereof. Antibodies and immunoassays can be carried out as identified above. In a preferred aspect of this invention, a polypeptide for incorporation into a vaccine composition consists essentially of (A) the amino acid sequence set out in SEQ ID NO. 2 or (B) a variant sequence thereof or (C) a fragment of either sequence. In general, the naturally occurring R28 amino acid sequence shown in SEQ ID NO. 2 or a fragment thereof is preferred.

A variant for incorporation in a vaccine composition which may be used against *S. pyogenes* or Group B *Streptococcus* or both is one which will react with anti-R28 antibodies, anti-Rib antibodies, anti-Rib-like protein antibodies or all of these antibodies. Over the entire length of SEQ ID NO. 2, a variant will preferably be at least 80% homologous to that sequence based on amino acid identity. Preferably, the polypeptide is at least 85 or 90% and more preferably at least 95, 97 or 99% homologous to SEQ ID NO. 2 over the entire region.

Fragments of the protein for formulation in a vaccine composition preferably includes the region beginning at position 87 in SEQ ID NO. 2 and may extend at least to position 229. Variants of this region will preferably be at least 70%, preferably at least 80% or 90% and more preferably 95% homologous to this region, based on amino acid identity. Alternatively, or in addition the polypeptide may comprise the segment beginning at position 230 of SEQ ID NO. 2 extending up to position 424 of SEQ ID NO. 2. Variants of this region will preferably be at least 70% preferably at least 80 or 90% and more preferably 95% homologous to this region.

Preferably, the vaccine composition includes part or all of at least one repeat, having the sequence of SEQ ID NO. 3. Preferably, the polynucleotide has two or more such repeats. A variant of this polypeptide is preferably at least 97, 98 or 99% homologous to a sequence of SEQ ID NO: 3 over the entire length. All references to percentage homology are based on amino acid identity.

Amino acid substitutions may be made to SEQ ID NO. 2 or 3 for example, from 1, 2 or 3 to 10, 20 or 30 substitutions. The modified polypeptide retains the ability to generate an immune response and preferably will confer protective immunity to Group A Streptococcus, Group B Streptococcus or both. Conservative substitutions may be made, for example, according to Table 1 above. Amino acids in the same block in the second column and preferably in the same line in the third column may be substituted for each other.

One or more amino acids may be alternatively or additionally added to any one of the polypeptides described above in accordance with the various aspects of the invention. An extension may be provided at the N-terminus or C-terminus of the sequence of SEQ ID No 2 or 3 or polypeptide variant or fragment thereof. The length of each extension may be quite short, for example from 1 to 10 amino acids in length. Alternatively, the extension may be longer, and another protein may be fused to an amino acid sequence according to the invention. A fusion protein incorporating the polypeptides described above can thus be provided.

In a further aspect the invention provides a polypeptide having the amino acid sequence of SEQ ID No 2 or any variant thereof as described herein.

Polypeptides of the invention may be in a substantially isolated form. It will be understood that the polypeptide may be mixed with carriers or diluents which will not interfere with the intended purpose of the polypeptide and still be regarded as substantially isolated. A polypeptide of the invention may also be in a substantially purified form, in which case it will generally comprise the polypeptide in a preparation in which more than 90%, e.g. 95%, 98% or 99% by weight of the polypeptide in the preparation is a polypeptide of the invention.

Polypeptides for incorporation in the vaccine composition of the invention may be modified for example by the addition of histidine residues to assist their identification or purification or by the addition of a signal sequence to promote their secretion from a cell where the polypeptide does not naturally contain such a sequence.

A polypeptide of the invention above may be labelled with a revealing label. The revealing label may be any suitable label which allows the polypeptide to be detected. Suitable labels include radioisotopes e.g. $^{125}$I, $^{35}$S, enzymes, antibodies, polynucleotides and linkers such as biotin. Labelled polypeptides of the invention may be used in diagnostic procedures such as immunoassays in order to determine the amount of a polypeptide of the invention in a sample.

Polypeptides or labelled polypeptides of the invention may be used in serological or cell mediated immune assays for the detection of immune reactivity to said polypeptides in animals and humans using standard protocols. The labelled polypeptide may be used to identify and/or isolate "accessory" proteins which are involved in binding between cell receptors and R28, by detecting the interaction of R28 with such proteins.

A polypeptide or labelled polypeptide of the invention or fragment thereof may also be fixed to a solid phase, for example the surface of an immunoassay well or dipstick.

Such labelled and/or immobilized polypeptides may be packaged into kits in a suitable container optionally including additional suitable reagents, controls or instructions and the like. The kits may be used to identify components that interact with R28.

Such polypeptides and kits may also be used in methods of detection of antibodies to the R28 protein by immunoassay.

Immunoassay methods are well known in the art and will generally comprise:
(a) providing a polypeptide comprising an epitope bindable by an antibody against said protein;
(b) incubating a biological sample with said polypeptide under conditions which allow for the formation of an antibody-antigen complex; and
(c) determining whether antibody-antigen complex comprising said polypeptide is formed.

Polypeptides of the invention may be made by synthetic means or recombinantly, as described below.

The polypeptides of the invention may be introduced into a cell by in situ expression of the polypeptide from a recombinant expression vector. The expression vector optionally carries an inducible promoter to control the expression of the polypeptide.

Such cell culture systems in which polypeptides of the invention are expressed may be used in assay systems.

A polypeptide of the invention can be produced in large scale following purification by high pressure liquid chromatography (HPLC) or other techniques after recombinant expression as described below.

Polynucleotides

A polynucleotide of the invention is capable of hybridising selectively with the coding sequence of SEQ ID No. 1 or to the sequence complementary to that coding sequence. Polynucleotides of the invention include variants of the coding sequence of SEQ ID No. 1 which encode the amino acid sequence of SEQ ID No.2 due to the degeneracy of the nucleic acid code, and variants which are recognized by antibodies to R28 or by antibodies produced against the purified protein of SEQ ID NO:2. Typically, a polynucleotide of the invention is a contiguous sequence of nucleotides which is capable of selectively hybridizing to the coding sequence of SEQ ID. No. 1 or to the complement of that coding sequence.

A polynucleotide of the invention hybridizing to the coding sequence of SEQ ID No. 1 can hybridize at a level significantly above background. Background hybridization may occur, for example, because of other DNAs present in a DNA library. The signal level generated by the interaction between a polynucleotide of the invention and the coding sequence of SEQ ID No. 1 is typically at least 10 fold, preferably at least 100 fold, as intense as interactions between other polynucleotides and the coding sequence of SEQ ID No. 1. The intensity of interaction may be measured, for example, by radiolabelling the probe, e.g. with $^{32}$P. Selective hybridization is typically achieved using conditions of medium to high stringency (for example 0.03M sodium chloride and 0.03M sodium citrate at from about 50° C. to about 60° C.).

A nucleotide sequence capable of selectively hybridizing to the DNA coding sequence of SEQ ID NO: 1 or to the sequence complementary to that coding sequence will be generally at least 70%, preferably at least 80 or 90% and more preferably at least 95%, homologous to the coding sequence of SEQ ID NO: 1 or its complement over a region of at least 20, preferably at least 30, for instance at least 40, 60 or 100 or more contiguous nucleotides such as over the entire length of SEQ ID No: 1 or its complement. Methods of measuring polynucleotide homology are well known in the art. The UWGCG Package which provides the BESTFIT program can be used to calculate homology (identity), e.g.

on its default settings (Deveraux et al. Nucl. Acids. Res. 12, 387–395, 1984), for both polynucleotides or polypeptides.

Any combination of the above mentioned degrees of homology and minimum size may be used to define polynucleotides of the invention with the more stringent combinations (i.e. higher homology over longer lengths) being preferred. Thus for example a polynucleotide which is at least 80% homologous over 25, preferably over 30 nucleotides forms one aspect of the invention, as does a polynucleotide which is at least 90% homologous over 40 nucleotides. A polynucleotide of the invention does not encompass a polynucleotide which is the Rib gene or a fragment thereof and preferably does not encode protein Rib or a fragment thereof.

Preferred polynucleotides which do not encode full length R28 are polynucleotides which encode regions of the protein commencing at asparagine at amino acid position 32 of FIG. 1A, and preferably the region from amino acid 32 to proline at position 173 inclusive. This corresponds to the region commencing with asparagine at amino acid position 88 in SEQ ID No 1 and preferably extends through to proline at position 229.

Polynucleotides encoding the region from amino acid 32 through to 173 of fig 1A will preferably be at least 70% and preferably at least 80 or 90% and more preferably 95% homologous with the relevant region of SEQ ID NO: 1. Polynucleotide of the invention may also include the region encoding aspartic acid at position 230 through to lysine at position 424 of SEQ ID NO. 1.

Polynucleotides hybridizing to the encoded repeat region of protein R28 will preferably be at least 96 and more preferably 97, 98 up to 99% homologous to the region of SEQ ID No 1 encoding SEQ ID No 3 that is the repeated sequence, the first repeat comprising amino acid positions 425 to 503 inclusive of SEQ ID No 1.

Preferred polynucleotides of the invention encode the amino acid sequence (A), (B) or (C) above. Polynucleotides of the invention may comprise DNA or RNA. They may also be polynucleotides which include within them synthetic or modified nucleotides. A number of different types of modification to polynucleotides are known in the art. These include methylphosphate and phosphorothioate backbones, addition of acridine or polylysine chains at the 3' and/or 5' ends of the molecule. For the purposes of the present invention, it is to be understood that the polynucleotides described herein may be modified by any method available in the art.

Polynucleotides of the invention may be used to produce a primer, e.g., a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as a DNA polynucleotide and primers according to the invention may be produced recombinantly, synthetically, or by any means available to those of skill in the art. They may also be cloned by standard techniques. The polynucleotides are typically provided in isolated and/or purified form.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using PCR (polymerase chain reaction) cloning techniques. This will involve making a pair of primers (e.g. of about 15–30 nucleotides) to a region of the spr28 gene which it is desired to clone, bringing the primers into contact with DNA obtained from a bacterial cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Such techniques may be used to obtain all or part of the spr28 gene sequence described herein.

Although in general the techniques mentioned herein are well known in the art, reference may be made in particular to Sambrook et al. Molecular Cloning: A Laboratory Manual. 1989.

Polynucleotides or primers of the invention may carry a revealing label. Suitable labels include radioisotopes such as $^{32}$P or $^{35}$S, enzyme labels, or other protein labels such as biotin. Such labels may be added to polynucleotides or primers of the invention and may be detected using techniques known per se.

Polynucleotides or primers of the invention or fragments thereof, labelled or unlabelled, may be used by a person skilled in the art in nucleic acid-based tests for detecting or sequencing spr28 in a sample.

Such tests for detecting generally comprise bringing a sample containing DNA or RNA into contact with a probe comprising a polynucleotide or primer of the invention under hybridizing conditions and detecting any duplex formed between the probe and nucleic acid in the sample. Such detection may be achieved using techniques such as PCR or by immobilizing the probe on a solid support, removing nucleic acid in the sample which is not hybridized to the probe, and then detecting nucleic acid which has hybridized to the probe. Alternatively, the sample nucleic acid may be immobilized on a solid support, and the amount of probe bound to such a support can be detected.

The probes of the invention may conveniently be packaged in the form of a test kit in a suitable container. In such kits the probe may be bound to a solid support where the assay formats for which the kit is designed requires such binding. The kit may also contain suitable reagents for treating the sample to be probed, hybridizing the probe to nucleic acid in the sample, control reagents, instructions, and the like.

Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and crowing the host cell under conditions which bring about replication of the vector. The vector may be recovered from the host cell. Suitable host cells as described below in connection with expression vectors.

Preferably, a polynucleotide of the invention in a vector is operably linked to a control sequence which is capable of providing for the expression of the coding sequence by the host cell, i.e. the vector is an expression vector. Such expression vectors can be used to express the R28 protein for incorporation in the vaccine compositions of the invention.

The term "operably linked" refers to a juxtapositions wherein the components described are in a relationship permitting them to function in their intended manner. A control sequence "operably linked" to a coding sequence is ligated in such a way that expression of the coding sequence is achieved under conditions compatible with the control sequences.

Such vectors may be transformed into a suitable host cell as described above to provide for expression of a polypeptide or polypeptide fragment of the invention. Thus, in a further aspect the invention provides a process for preparing a polypeptide or polypeptide fragment according to the invention, which process comprises cultivating a host cell transformed or transfected with an expression vector as described above under conditions to provide for expression of the polypeptide or fragment, and recovering the expressed polypeptide or fragment.

The vectors may be for example, plasmid, virus or phage vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid.

A further embodiment of the invention provides host cells transformed or transfected with the polynucleotides or vectors for the replication and expression of polynucleotides of the invention. The cells will be chosen to be compatible with the said vector and preferably will be bacterial. Host cells may also be cells of a non-human animal, or a plant transformed with a polynucleotide of the invention.

Promoters and other expression regulation signals may be selected to be compatible with the host cell for which the expression vector is designed.

Vaccine Formulation

Typically, the vaccines are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredient may be mixed with an excipient which is pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine.

Examples of adjuvants which may be effective include but are nor limited to: aluminium hydroxide. N-acetyl-muramyl-L-threonyl-D-isoglutamin (thr-MDP). N-acetyl-nor-muramyl-L-alanyl-D-isoglutamine (CGP 11637, referred to as nor-MDP), N-acetylmuramyl-L-alanyl-D-isoglutamnyl-L-alanine-2-(1'-2'-dipalmitovl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against an immunogenic polypeptide containing R28 antigenic sequence resulting from administration of this polypeptide in vaccines which are also comprised of the various adjuvants.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides: such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccarine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. as a suspension. Reconstitution is preferably effected in buffer.

Capsules, tablets and pills for oral administration to a patient may be provided with an enteric coating comprising, for example. Eudragit "S", Eudragit "L", cellulose acetate, cellulose acetate phthalate or hydroxypropylmethyl cellulose.

The polypeptides of the invention may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric and maleic. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol histidine and procaine.

Vaccine Administration

The vaccines are administrated in a manner compatible with the dosage formulation and in such amount as will be prophylactically effective. The quantity to be administered, which is generally in the range of 100 kg to 100 mg, preferably 200 µg to 10 mg of antigen per dose, depends on the subject to be treated, capacity of the subject's immune system to synthesize antibodies, and the degree of protection desired. Precise amounts of active ingredient required to be administered may depend on the judgement of the practitioner and may be peculiar to each subject.

The vaccine may be given in a singe dose schedule, or preferably in a multiple does schedule. A multiple dose schedule is one in which a primary course of vaccination may be with 1–10 separate doses, followed by other doses given at subsequent time intervals required to maintain and or reinforce the immune response, for example at 1 to 4 months for a second dose, and if needed, a subsequence dose(s) after several months. The dosage regimen will also, at least in part, be determined by the need of the individual and be dependent upon the judgement of the practitioner.

The following Examples illustrate the invention.

EXAMPLE 1

Sequencing of the Gene Encoding R28, spr28

Preliminary immunochemical work indicated that R28 is related to the GBS proteins a and Rib. Thus sequencing of spr28 was based on the known sequences of the genes encoding these protein, the bca and rib genes Michel et al, Proc Natl Acad Sci. 1992, 89, 10060–10064 and Wästfelt et al. J. Biol Chem, 1996, 271, 18892–18897. Primers derived from bca and rib were used to PCR amplify different regions of spr28 from chromosomal DNA of strain AL368, an R28-expressing *S. pyogenes* strain of type M28. The PCR primers were derived from sequences present upstream and downstream of the bca and rib genes, from the region encoding the N-terminus of α, and from the repeat regions of rib. Additional primers were derived from new sequences identified in spr28. PCR products were subcloned into plasmid pGEM7Z(f+) and products from at least three independent reactions were sequenced with the Thermo Sequenase dye terminator cycle kit pre-mix and an automatic DNA-sequenator.

The highly repetitive region of spr28 caused difficulties during sequences. The total number of repeats in the repeat region was determined from the size of a PCR product covering the entire repeat region and also from the number of sites in the characteristic ladder pattern obtained in the PCR. For each end of the repeat region, amplification with one primer outside and one primer inside the repeat region yielded PCR products containing one or more repeats, due to priming at different sites in the repeat region. Sequencing of such PCR products yielded the sequences of the first one and a half repeats and of the two last repeats. The remaining repeats were analyzed by cloning repeats at random. PCR was performed with primers internal to the repeat region, and products corresponding to 0.9 and 1.9 repeats were recovered. Determination of nucleotide sequences for a total of 12 repeats did not disclose any differences between these repeats and those located at the ends of the repeat region. Thus, all repeats in spr28 are most likely identical. The sequence of spr28 is set out in SEQ ID NO 1.

EXAMPLE 2

Figure 1B:
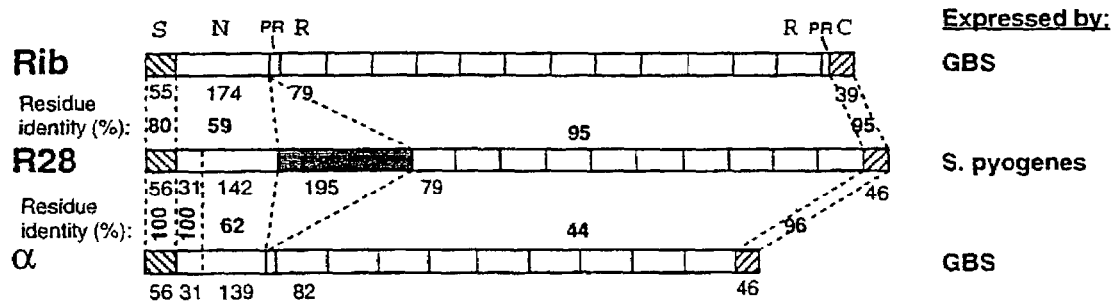
FIG. 1. Analysis of the sequence of the R28 protein: comparison with surface proteins from group B streptococcus (GBS). (A) Alignment of the amino acid sequence of R28 with those of the Rib and α proteins of GBS. (B)

Comparison of the R28 Protein to Several Group B *Streptococcal* Surface Proteins The alignment of R28 with those of Rib and α proteins is shown in FIG. 1A. The arrows indicate the ends of the signal sequences. For R28, this position was identified by determination of the NH$_2$-terminal sequence (12 residues) of the purified protein. Regions with identical repeats are boxed. Only one full repeat from each protein is shown. The positions of partial repeats are indicated. As a result of the alignment used here, the repeats in Rib and α have sequences that are permuted, as compared to those in the original publications. The non-repeated region of R28 includes a 195-residue region, described below, which did not fit into the alignment shown here. The overall structure is shown in FIG. 1B. S, signal peptide: N, non repeated NH$_2$-terminal region; PR, partial repeat: R, one repeat: C, COOH-terminal region. The figures indicate the number of amino acids in each region and percent residue identity between corresponding regions. The shaded area in R28 represents the region that is not aligned with the other proteins in FIG. 1A.

R28, Rib and α have similar overall structure (FIGS. 1A and 1B), with an unusually long signal peptide (55 or 56 aa residues), a non-repeated NH$_2$-terminal region, 9–12 identical repeats of ~80aa, and a COOH-terminal region probably used for cell wall anchoring. There are 10 identical 79-residue repeats in the R28 protein studied here. Alignment of the three sequences demonstrates extensive residue identity, but in the long NH$_2$-terminal region of R28 there is one region (shaded in FIG. 1B) that does not fit into the alignment. The processed form of the R28 protein has a total length of 1204 amino acid residues and a deduced molecular weight of 126,890.

Figure 1C:
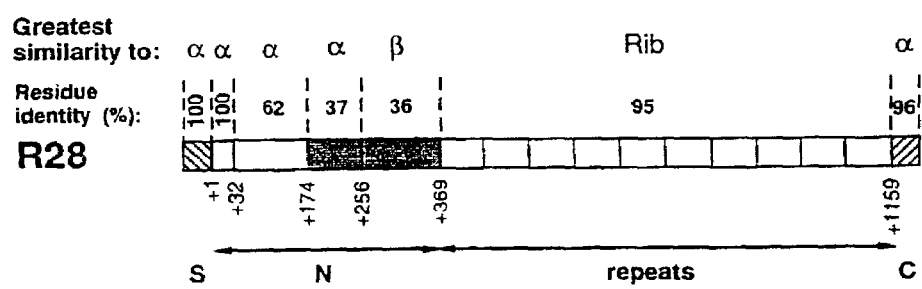

The R28 protein can be divided into several different regions, based on residue identity to other proteins (FIG. 1C). For each subregion, the number of the first amino acid in that region is indicated, based on the processed form of R28. The signal peptide and the first 31 aa resides in the NH$_2$-terminal region are identical to the corresponding region in α, and are followed by a 142-residue region showing 62% identity to α. The region indicated by shading can be divided into two subregions. The first of these subregions shows greatest identity (37%) to the repeat region of a and has the same length as one repeat. The second subregion lacks identity to Rib or α but shows 36% identity to another surface protein of GBS, the IgA-binding βprotein, which is structurally unrelated to Rib and α. The repeats of R28 are similar to those in Rib.

EXAMPLE 3

Purification of R28 and Other *Streptococcal* Surface Proteins

R28 was purified from *S. pyogenes* strain AL368. A mutanolvsin extract was prepared from the bacteria in a 10 l overnight culture of AL368, and R28 was purified by two steps of DEAE ion exchange chromatography followed by gel filtration on a column of Sepharose CL6B (Pharmacia, Uppsala, Sweden). The presence of R28 in different fractions was monitored by Western blot analysis, using an antiserum raised against *S. pyogenes* bacteria expressing the R28 and T28 antigens from the Institute of Sera and Vaccines Prague. Czech Republic. The R28 and T28 antigens are most likely identical. The analysis with this antiserum identified a single 130 kD protein, supporting the conclusion that R28 is identical to T28. All fractions were also analyzed with antiserum raised against protein Rib from GBS. Both antisera identified the same protein, confirming that the purified protein was indeed R28 protein which cross-reacts with one or more GBS proteins. The final yield of purified R28 was ~10 mg.

The R28 protein extracted from *S. pyogenes* was compared in Western blots to highly purified preparations of the three GBS proteins Rib. αand β. The analysis employed rabbit antisera (diluted 1:1,000), raised against the purified proteins, and bound antibodies were identified by incubation with radiolabeled protein G, followed by autoradiography (data not shown). The three GBS proteins do not cross-react. R28 lacked cross-reactivity with the αand βproteins, but cross-reacted with Rib. Thus, R28 did not cross-react with α, in spite of the sequence identity between the two proteins in the most N-terminal region, suggesting that this region is poorly immunogenic. The cross-reactivity between R28 and Rib is readily explained by the substantial residue identity in the repeat region.

Since the R28 protein studied here had not been formally shown to be exposed on the bacterial surface, antiserum to the purified protein was used to test for surface expression (FIG. 2). Rabbit antiserum could not be used for this analysis, since the R28-expressing strain expresses surface M proteins that bind rabbit IgG-Fc. The analysis was therefore performed with mouse antibodies, which do not show Fc-reactivity with M proteins. Suspensions of the R28-positive *S. pyogenes* strain AL368 and the R28-negative strain AW43 were incubated with mouse anti-R28 serum, diluted as indicated. Bound antibodies were detected by the addition of radiolabeled protein A. Binding (%) refers to the fraction of added protein A bound. Controls with preimmune mouse serum were completely negative. As expected, R28 was present on the surface of the R28-expressing bacteria (strain AL368), but not on the negative control (strain AW43).

EXAMPLE 4

R28 Promotes Adhesion of *S. pyogenes* to Human Cervical Cells

The similarity between R28 and the Rib and α proteins of GBS suggested that these *streptococcal* surface proteins have similar functions, although they are expressed by pathogens that usually cause very different types of disease. The function of Rib and α in GBS infections is not known, but the fact that GBS is part of the normal flora of the human vagina suggested that Rib and α might function as adhesins and that they promote binding to epithelial cells in the vagina and/or cervix. R28 may therefore also act as an adhesin and expression of R28 may allow *S. pyogenes* to colonize the female genital tract which may explain why R28 strains are common among isolates from puerperal fever. We constructed an R28-negative mutant of *S. pyogenes* strain AL368 and compared this mutant and the parental strain for ability to adhere to human cervical cells.

The R28 negative mutant was constructed by replacing most of the spr28 gene, encoding R28, with a kanamycin resistance cassette. The procedure was based on the use of the *E. coli*-*S. pyogenes* shuttle vector pJRS233, in which replication is temperature-sensitive in *S. pyogenes*, allowing selection of recombinants arising through homologous recombination. A derivative of pJRS233 was constructed, in which the kanamycin resistance cassette ΩKm2 was flanked by sequences derived form the 5' and 3' regions of the rib gene of GBS. This derivative of pJRS233 was transformed into strain AL368. Since the 5' and 3' regions of the rib gene are almost identical to the corresponding regions of the spr28 gene, the ΩKm2 cassette could be introduced into the *S. pyogenes* chromosome by homologous recombination, resulting in a strain where the central repeat region of the spr28 gene has been replaced by ΩKm2. Absence of the spr28 gene in the mutant was verified by PCR.

Figure 3A:
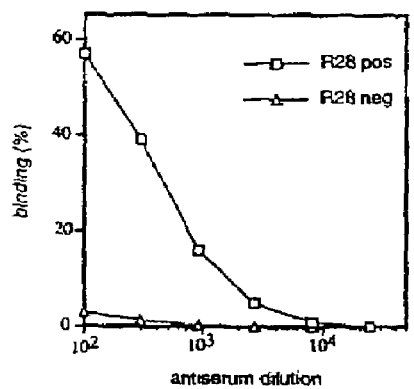

The growth rate in vitro of this mutant was not different from that of the parental strain. The mutant lacked surface expression of R28, as shown by analysis with mouse anti-R28 serum (FIG. 3A). Analysis performed with mouse anti-R28 serum, as described for FIG. 2. Mutanolvsin extracts of the R28-positive strain AL368 and its R28-negative mutant were analyzed by Western blot, using anti-R28 serum. The R28 band present in the AL368 extract is marked with a star. The R28 protein was absent from an extract of the mutant (data not shown). As expected, the two antiphagocytic M proteins expressed by the parental strain were expressed normally in the R28-negative mutant (data not shown).

The R28-expressing strain (AL368) and its R28-negative mutant were analyzed for ability to adhere to ME180, an epithelial cell line that originates from a human cervical carcinoma. The ME180 cell line (ATCC HTB33), derived from a human cervical carcinoma, was obtained from Dr. A-B Johnsson (Karolinska Institutet, Stockholm, Sweden) and maintained in Dulbecco's Modified Eagle's Medium (DMEM) supplemented with 6% fetal calf serum, 4 mM L-glutamine, 10 mM Hepes and 10 µg/ml gentamycin. The cells were grown in an atmosphere of 5% $CO_2$ and 95% air. For adherence assays, the cells were grown on plastic cover slips in 24-well plates for two days. New medium without gentamycin was then added, and the cells were used in the adherence assay next day. The cell layer was not confluent.

In the adherence assay, the ME180 cells were first pre-incubated for 30 mins at 37° C. with DMEM supplemented with 4 mM L-glutamine. 10 mM Hepes and 20% fresh human plasma heat-activated at 56° C. for 30 mins before use. After washing once with PBS, 1 ml of bacterial suspension ($10^7$ cfu) was added to each well and incubation continued at 37° C. for 2 h. The bacterial suspension had been prepared by washing bacteria from a stationary phase culture with PBS and resuspending them to $10^7$ cfu/ml in DMEM supplemented with 4 mM L-glutamine. 10 mM Hepes and 20% fresh heat-inactivated human plasma. The plasma was added to reduce background binding of bacteria to the coverslips. However, results qualitatively similar to those obtained with plasma were obtained in experiments without plasma.

After incubation with bacteria, the ME180 cells were washed x10 with PBS, fixed with 10% TCA for 3 mins and stained with Giemsa. The adherence of *streptococci* to ME180 was analyzed by light microscopy. The number of adhering *streptococcal* chains was determined for at least 200 ME180 cells in each experiment. Some chains of *S. pyogenes* have a tendency to clump. Only chains that appeared to adhere directly to a ME180 cell were counted. All experiments were independently evaluated by at least two different examiners, who obtained very similar results.

Figure 3B:
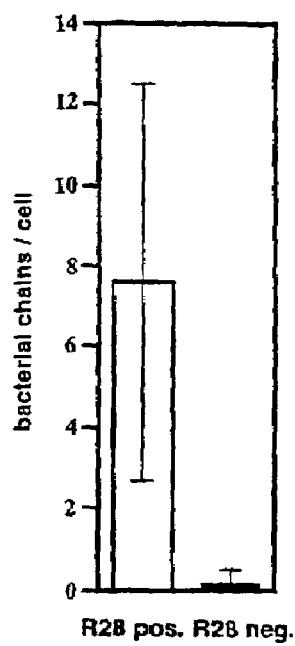

Strain AL368 adhered to the ME180 cells, but the R28-negative mutant did not (FIG. 3B). The figure shows the average number of streptococcal chains bound per ME180 cell, with standard deviations. The range (chains/cell) was 0–23 for the R28 positive strain and 0–3 for the mutant. The figure is based on data obtained in one out of four different experiments, all of which gave very similar results. At least 200 ME180 cells were analyzed in each experiment. Light microscopy showing that 2 D human ME180 cells bind the R28-positive parenteral strain AL368, but not its R28-negative mutant. *S. pyogenes* grows in chains and binding of AL368 to the epithelial cells was in many cases due to binding at one end of the chain while other chains adhered at multiple points. The lack of binding of the mutant was not due to an effect on chain length, which was similar (average ~7 bacteria per chain) in the mutant and in the parental strain. In the experiment shown in FIG. 3B, the average number of bacterial chains adhering to each epithelial cell was 7.6 for strain AL368 and 0.15 for the R28-negative mutant. Thus, the R28-mutation caused an ~50-fold reduction in adhesion to ME180 cells.

EXAMPLE 5

Antibodies to R28 Protect Against Lethal Infection

Early studies of the R28 protein indicated that antibodies to this protein do not protect mice against lethal infection with an R28-expressing strain of *S. pyogenes*. Lancefield and Perlmann *J. Exp. Med* 1952 96: 83–97. However, antibodies raised against the highly purified R28 protein described here protected mice against lethal infection with two different R28-expressing *S. pyogenes* strains (FIG. 4). C3H/HeN mice were injected i.p. with rabbit antiserum raised against purified R28, or with preimmune serum. Four h later, the mice were challenged i.p. with $4 \times 10^4$ cfu of the R28-expressing reference strain "Griffith small" obtained from Dr. E. Falsen Culture Collection of the University of Gothenburg Sweden or with $3 \times 10^7$ cfu of the R28-expressing puerperal fever isolate 2369–97 provided by Dr. Facklam (Centers for Disease Control, Atlanta Ga.). Deaths were recorded daily, as indicated. The final ratios (no. of surviving mice)/(no. of mice challenged) are indicated. The $\chi^2$ test was used for calculation of P value. The data shows that the R28 protein elicits protective immunity. The reason for the lack of protection in the earlier study is not known.

EXAMPLES 6–9

Materials and Methods

Bacterial Strains and Media

The R28-expressing GAS strains AL368 and "Griffith" have been described. AW43 is a GAS strain lacking R28. A collection of 14 R28 expressing GAS strains, isolated from cases of septicaemia, pharyngitis or puerperal fever, were available in our laboratory. The GBS type III strains BM110 and BS30 express Rib. The type Ib strain SB35, and its mouse virulent derivative SB35sedI. expresses the α and β proteins. The GBS type II strain 1954/92 was from Dr R. Facklam and the type II strain 118/158 was from Dr J. Jelinkova (National Institute of Public Health. Prague, Czechia). The GBS type III prototype strain D136C was from Dr J. Michel (Channing Laboratory, Boston. MA). The GBS type V strain 2471 was from Dr. G. Orefici (Istituo Superiore di Sanita, Rome, Italy). Additional Rib-expressing GBS strains of types II and III were available in our collections. Streptococci were grown in Todd-Hewitt broth (Oxoid, Basingstoke, Hampshire, UK) at 37° C., without shaking.

Purified Proteins, Antisera

R28 was purified from GAS strain AL368. Rib from GBS strain BM110, and β from GBS strain SB35. These highly purified protein preparations did not contain detectable amounts of contaminating proteins or polysaccharides. Antisera against the purified proteins were raised in rabbits and mice, using complete Freund's adjuvant.

Inhibition Test for Analysis of Cross-Reactivity

Microtiter plates (Falcon 3912, Becton Dickinson, Oxnard, Calif.) were coated with purified protein (R28 or Rib) by incubation for 16 h with 100 μl of a solution of protein (500 ng/ml) in PBS. The wells were blocked by washing three times with veronal-buffered saline (10 mM veronal buffer 0.15 M NaCl, pH 7.4) supplemented with 0.25% gelatin and 0.25% Tween 20. The binding of antibodies to the immobilized protein was inhibited with purified proteins or with whole bacteria. For inhibition tests with purified proteins, various amounts were mixed with 100 μl aliquots of antiserum in PBSAT (PBS supplemented with 0.02% sodium azide and 0.05% Tween-20) incubated for 30 min. and then added to the coated wells. The antisera were used at a final dilution corresponding to 80% of maximal binding. After incubation for 3 h, the wells were washed three times with PBSAT and bound antibodies were detected by the addition of $^{125}$I-labeled protein A or protein G (~15.000 cpm in 100 μl PBSAT for each well). Protein A was used for mouse antibodies and protein G for rabbit antibodies. After incubation for 2 h and three washes with PBSAT, the radioactivity of each well was determined in a γ-counter. Nonspecific binding (less than 1%) was determined in wells coated with buffer (PBS) alone, and has been subtracted. All incubations were performed at room temperature. For inhibition tests with whole bacteria, washed suspensions of bacteria in PBSAT were used instead of purified proteins.

Since protein A and protein G were used in the tests described above, these tests measured cross-reactive IgG antibodies. Protein A may also detect some IgM molecules, but the mouse sera used did not contain detectable IgM against the proteins studied here, as measured by ELISA.

Protection of Mice by Active and Passive Immunization

For active immunization with purified R28, mice (male C3H/HeN, age 8–10 weeks) were vaccinated s.c. with 25 μg of protein in CFA, and boosted 4 weeks later with the same amount in incomplete Freund's adjuvant. Control mice received BSA. Two weeks after the booster, the mice were challenged by i.p. injection with an ~$LD_{90}$ dose of log-phase bacteria, and deaths were recorded daily for one week. Two mice in each group were not challenged, but were bled for analysis of antibody responses by ELISA. Active immunization with purified Rib was performed in the same way, but without adjuvant, and control mice received PBS.

For active immunization of mice with whole living GAS, washed suspensions (150 μl) containing $10^7$ cfu of washed stationary phase bacteria in PBS were injected s.c. Two identical injections were given with a 4 week interval. The mice were challenged i.p. two weeks later with an ~$LD_{90}$ dose of GBS strain BM 110. Two mice were not challenged, but were bled for analysis of antibodies to R28.

For passive immunization, mice were injected i.p. with 100 μl of rabbit antiserum (diluted in PBS to a total volume of 0.5 ml), and challenged 4 h later by i.p. injection of an ~$LD_{90}$ dose of bacteria, as described above.

Other Methods

Mutanolysin extracts of streptococci were prepared as described Stalhammar-Carlemalm et al J. Exp. Med 1993 177 1593–603. Proteins were radiolabeled with carrier-free $^{125}$I (Amersham International, Amersham, Bucks, UK) by the chloramine T method. Total protein concentrations were determined with the Micro BCA reagent (Pierce, Rockford, Ill.). Determination of specific antibodies by ELISA was performed as described Larsson et al Infect Immun 1996 64 3518–23. Western blots and analysis of bacteria for surface expression of proteins were performed as described Stalhammar-Carlernalm supra. The Fisher exact test was used for statistical analysis.

EXAMPLE 6

Immunological Comparison of the R28 and Rib Proteins

Figure 5A:
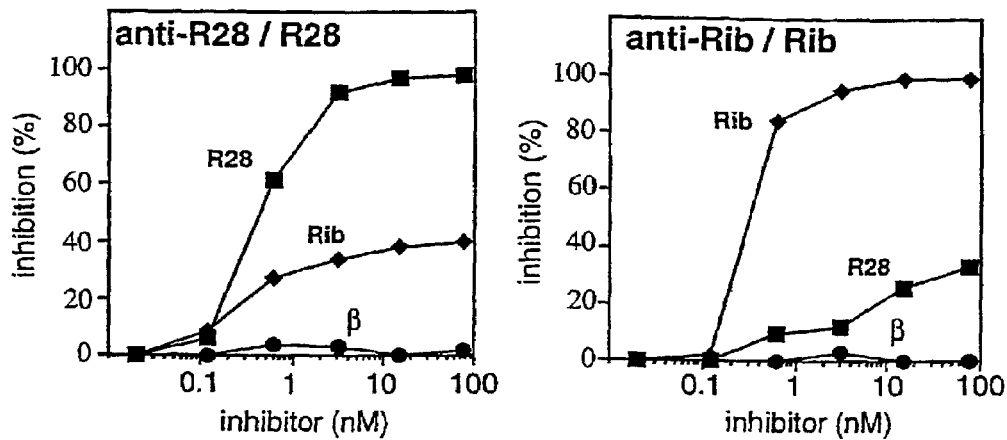

Features of R28 and Rib relevant to this study are summarised in FIG. 1. The purified R28 and Rib proteins cross-react, when analyzed by Western blot as described in Example 3 above. The cross-reactivity of IgG antibodies to these proteins was analyzed in inhibition experiments, in which the binding of antibodies to immobilized protein was inhibited by the addition of purified proteins (FIG. 5A). The binding of anti-R28 to R28 could be completely inhibited by the addition of highly purified R28, but addition of purified Rib did not cause more than ~40% inhibition even at the highest concentration tested (FIG. 5A, left panel). Thus, ~60% of the anti-R28 antibodies did not recognize Rib under the conditions used here. Moreover, most of those anti-R28 antibodies that recognized Rib had higher affinity for R28 than for Rib, as shown by the more rapid increase for the R28 curve in the interval between 0.1 nM and 1 nM inhibitor. Addition of β protein did not cause any inhibition, in agreement with the lack of cross-reactivity between R28 and β in Western blot analysis. Inhibition tests were also performed, in which the binding of anti-Rib to Rib was inhibited with the different purified proteins (FIG. 5A, right panel). The results were similar to those described above, but the difference in inhibitory capacity between R28 and Rib was even more pronounced in this case. The results of these inhibition tests were not due to unusual properties of the rabbit antisera used, since similar results were obtained with mouse sera (data not shown). Taken together, these data show that the sequence differences between R28 and Rib have major effects on the immunological properties of the purified proteins.

Figure 5B:
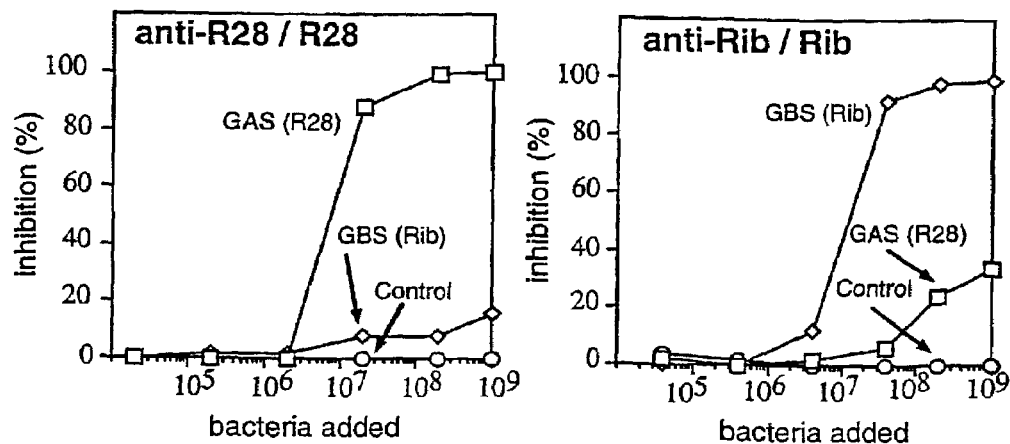

Inhibition tests were also performed to analyze the cross-reactivity of R28 or Rib expressed on the surface of whole bacteria (FIG. 5B). In these tests, washed suspensions of whole bacteria were added to a test system similar to that described above. However, mouse antisera were used, rather than rabbit antisera, to avoid interactions with GAS surface proteins (M proteins) that bind rabbit IgG-Fc. The binding of anti-R28 to R28 was completely inhibited by R28 expressing GAS, but was inhibited only poorly by Rib-expressing GBS (FIG. 5B, left panel). Similar results were obtained when the binding of anti-Rib to Rib was inhibited with whole bacteria (FIG. 5B, right panel). These data cannot be explained by quantitative differences in surface expression of Rib and R28, but indicate that the two proteins show major antigenic differences, in agreement with the results obtained with purified proteins (FIG. 5A).

EXAMPLE 7

Antibodies Against R28 or Rib Confer Cross-Protection

Figure 6B:
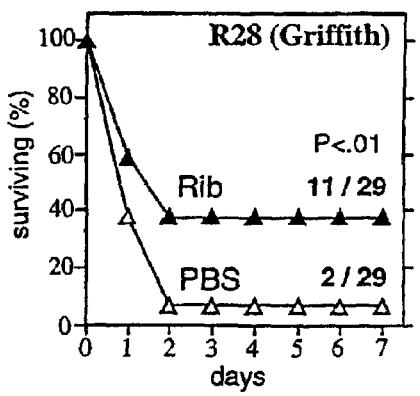
Figure 6C:
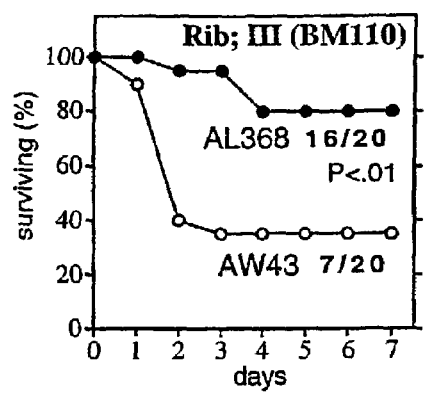
Figure 6A:
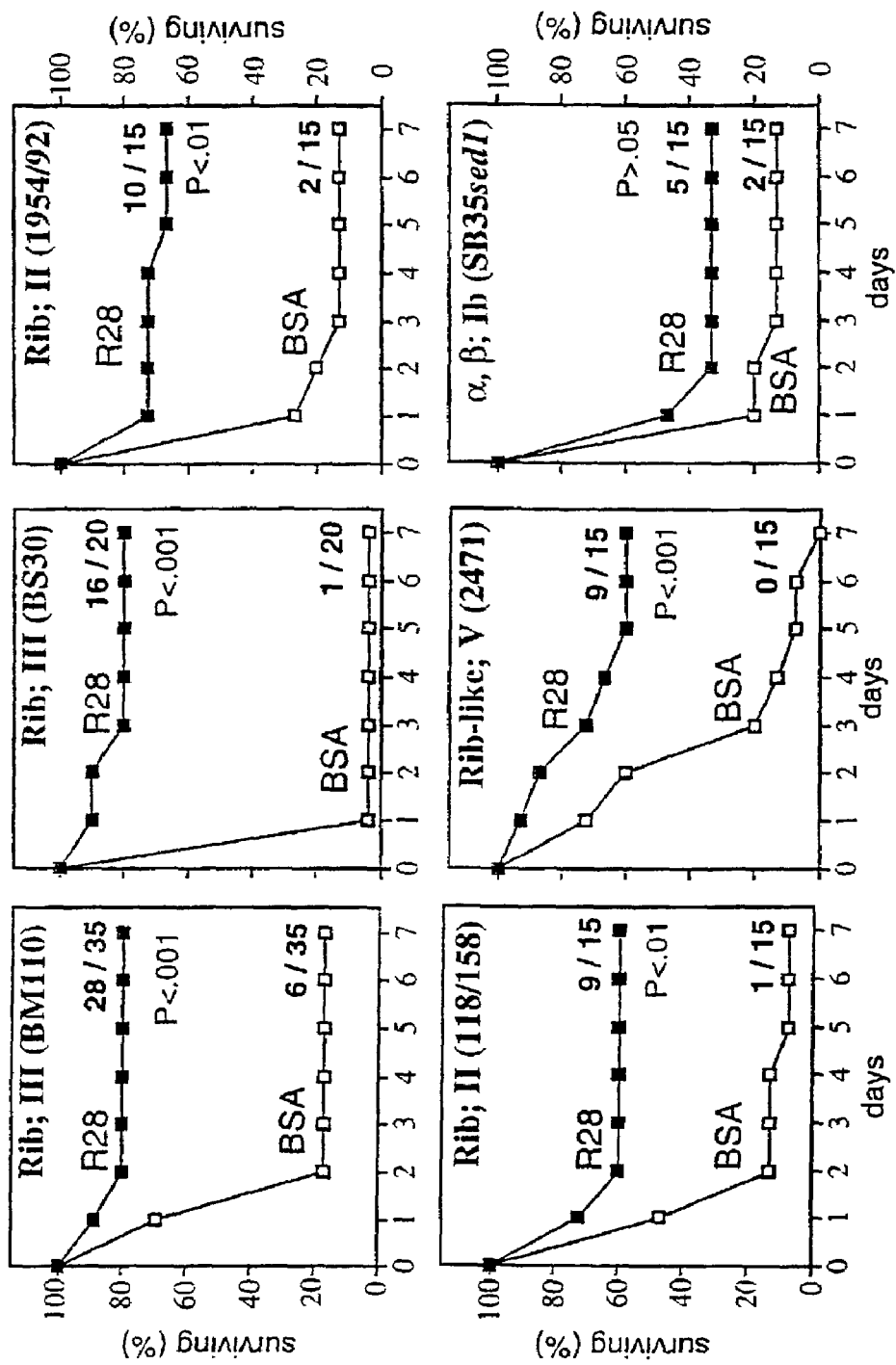

Mice were immunized with highly purified R28 protein, or with BSA as a control, and the immunized mice were tested for immunity to lethal GBS infection (FIG. 6A). The GBS strains studied represented four different capsular serotypes. Immunization with R28 protected against two Rib-expressing GBS strains of type III and against two Rib-expressing GBS strains of type II. All four of these GBS strains express Rib proteins that appear to be immunologically identical (see below). In addition, immunization with R28 protected against a type V strain expressing a "Rib-like" protein (see below). In contrast, immunization with R28 did not confer significant protection against infection with a type Ib GBS strain expressing the α and β proteins, which do not crossreact with R28.

Immunization with pure Rib protected mice against lethal infection with an R28-expressing GAS strain, i.e. Rib also conferred cross-protection (FIG. 6B). The GAS strain used to sequence and purify R28, strain AL368, could not be used for challenge in this experiment, since it lacked mouse virulence. However, the R28-expressing strain used (strain "Griffith") expresses an R28 protein that appears to be immunologically identical to that of strain AL368 (see below). Moreover, extensive PCR analysis did not demonstrate any difference in sequence between the R28 proteins expressed by these two GAS strains (data not shown).

The mice immunized with R28 or Rib showed good IgG antibody responses, as measured by ELISA. No IgM antibodies directed against Rib or R28 could be detected in these sera (data not shown).

The crossprotection conferred by R28 and Rib was further analyzed in a passive immunization model employing rabbit antisera (Table 2). Previous work with this model showed that anti-R28 and anti-Rib protected mice against lethal infection with strains expressing the homologous protein. The data reported here show that anti-R28 protected against lethal infection with a Rib-expressing GBS strain, and that anti-Rib protected against a R28-expressing GAS strain.

Thus, cross-protection could be demonstrated both in active and in passive immunization models, and humoral immunity is sufficient for this cross-protection.

TABLE 2

Passive immunization of mice with rabbit antiserum to R28 or Rib confers cross-protection

| | | Relevent cell surface protein | Mice surviving after pretreatment with | | |
|---|---|---|---|---|---|
| | Strain | | anti-R28 serum | anti-Rib serum | normal serum |
| GBS | BM110 | Rib | 11/21[b] | | 1/23 |
| GAS | Griffith | R28 | | 15/22[b] | 4/22 |

[a]C3H/HeN mice were injected i.p. with 0.1 ml rabbit antiserum (diluted to 0.5 ml with PBS) and challenged 4 h later by i.p. injection of an $\sim ID_{90}$ dose of bacteria. Deaths were recorded daily for seven days. All deaths occurred within 48 h. The survival data were analyzed by the Fisher exact test.
[b]$P < 0.001$. compared to the mice that received normal serum.

EXAMPLE 8

Infection with Living R28-Expressing Bacteria Causes Cross-Protection

The immunization experiments suggested that cross-protection may occur also after immunization by infection with living bacteria. For analysis of this hypothesis, mice were infected s.c. with sublethal doses of an R28-expressing GAS strain, or with control GAS not expressing R28, and subsequently challenged i.p. with a Rib-expressing GBS strain. The infection with the R28 expressing GAS strain caused significant protection against the GBS strain (FIG. 6C).

The mice infected s.c. with the R28-expressing GAS strain had IgG antibodies to R28 at the time of challenge with GBS, but no IgM was detectable. Interestingly, the titer of anti-R28 in these infected mice was as high as in mice immunized with pure R28 in Freund's adjuvant (data not shown).

It was not possible to perform cross-protection tests, in which mice were first infected s.c. with Rib-expressing GBS and then challenged with GAS, since s.c. infection with sublethal doses of GBS did not elicit antibodies to Rib (data not shown).

EXAMPLE 9

Characterization of R28 and Rib Proteins Expressed by Different Clinical Isolates Since the R28 protein studied here, purified from strain AL1368, conferred cross-protection, it was of interest to analyze whether R28 proteins expressed by different GAS isolates have similar immunological properties. Similarly, it was of interest to analyze whether all GBS strains classified as Rib-positive express immunologically similar proteins.

Figures 7A, 7B, 7C:
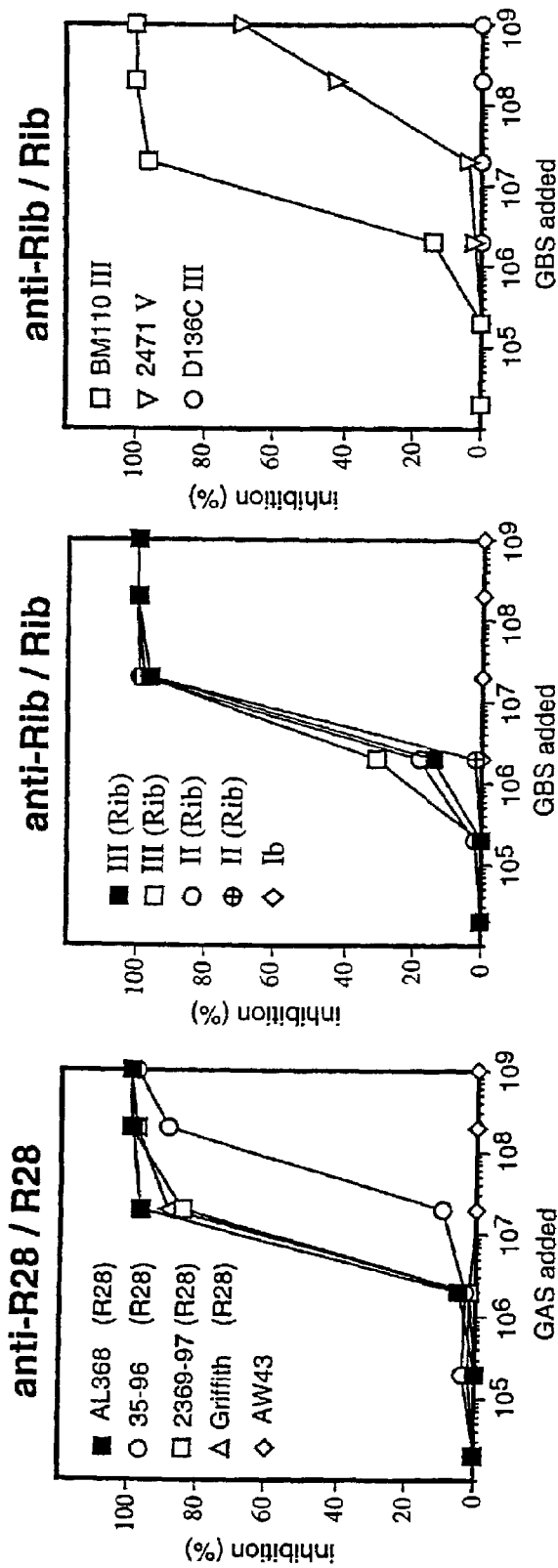

For comparison of R28 expressed by different GAS strains, whole R28-expressing bacteria were analyzed for ability to inhibit the reaction between R28, purified from strain AL368, and mouse antiserum raised against this purified protein. In this inhibition test, strain AL368 caused complete inhibition, while a strain lacking R28 did not cause any inhibition (FIG. 7A). Among 14 different R28-expressing strains analyzed, all caused complete inhibition of binding, indicating that they express R28 proteins that are immunologically very similar, if not identical, to that expressed by strain AL368. Inhibition data for three of these R28-expressing strains are shown in FIG. 7A. For unknown reasons, two of the 14 R28-expressing strains were less efficient than strain AL368 in causing inhibition, but complete inhibition was obtained also with these strains. Data for one of these two strains (35–96) are included in FIG. 7A.

The immunological relationship between proteins expressed by different GBS strains classified as Rib-positive was analyzed in inhibition tests with Rib (purified from strain BM110) and rabbit antiserum to this purified protein. Controls showed that strain BM110 caused complete inhibition, while a GBS strain lacking Rib did not cause any inhibition (FIG. 7B). Inhibition tests with 16 strains of capsular types III or II caused complete inhibition, indicating that they express Rib proteins that are immunologically similar, if not identical. Data for three of these strains are included in FIG. 7B.

Although the data reported above did not identify any differences between Rib proteins expressed by the clinically important GBS of types III and II, further analysis indicated that some GBS strains express a Rib-related protein that is not immunologically identical to Rib. One of these strains is the GBS type V strain 2471. In the inhibition analysis, this strain caused only partial inhibition (FIG. 7C), indicating that it may not express a typical Rib protein. Indeed, purification and preliminary characterization of the protein expressed by this type V strain has shown that it is not identical to Rib, and it is referred to here as "Rib-like". Importantly, immunization with purified R28 conferred protection against the type V strain expressing this Rib-like protein (FIG. 6A).

A second GBS strain giving an atypical result in the inhibition test was D136C a commonly used reference strain for GBS of capsular type III. This type III strain has been shown to express a protein that is immunologically related to the R-28 protein suggesting that D136C might express Rib. However, the protein expressed by D 136C is not Rib, since D136C bacteria completely lacked activity in the inhibition test with anti-Rib serum (FIG. 7C).

We claim:

1. A substantially isolated and purified polypeptide
   (i) comprising the amino acid sequence of SEQ ID No. 2; or
   (ii) consisting of the amino acid sequence of from residue 87 through to 229 of SEQ ID No. 2 or at least ten contiguous residues thereof, capable of inducing an immune response to a R28-expressing strain of S. pyogenes; or
   (iii) consisting of the amino acid sequence of from residue 230 through to 424 of SEQ ID No. 2 or at least ten contiguous residues thereof, capable of inducing an immune response against a R28-expressing strain of S. pyogenes; or
   (iv) consisting of the amino acid sequence of from residue 425 to 503 of SEQ ID No. 2.

2. A substantially isolated and purified polypeptide according to claim 1, wherein said polypeptide comprises SEQ ID No.2.

3. A substantially isolated and purified polypeptide according to claim 1, wherein said polypeptide consists of residues from 87 to 229 of SEQ ID No. 2.

4. A substantially isolated and purified polypeptide according to claim 1, wherein said polypeptide consists of residues from 230 to 424 of SEQ ID No. 2.

5. A substantially isolated and purified polypeptide according to claim 1, wherein said polypeptide consists of residues from 425 to 503 of SEQ ID No. 2.

6. A substantially isolated and purified polypeptide according to claim 1, wherein said polypeptide consists of at least ten contiguous residues of residues from 87 to 229 of SEQ ID No. 2, capable of inducing an immune response to a R28-expressing strain of S. pyogenes.

7. A substantially isolated and purified polypeptide according to claim 1, wherein said polypeptide consists of ten contiguous residues of residues from 230 to 424 of SEQ ID No. 2, capable of inducing an immune response to a R28-expressing strain of S. pyogenes.

8. A vaccine composition against a R28-expressing strain of S. pyogenes comprising a pharmaceutically acceptable carrier and a polypeptide which is encoded by the nucleotide sequence of SEQ ID No. 1.

9. A vaccine composition against a R28-expressing strain of S. pyogenes comprising a polypeptide comprising the amino acid sequence of SEQ ID No. 2 together with a pharmaceutically acceptable carrier.

10. A method of vaccinating a subject against an R28-expressing strain of S. pyogenes, comprising administering to said subject an effective amount of a polypeptide comprising the amino acid sequence of SEQ ID No. 2.

11. A method of vaccinating a subject against a R28-expressing strain of S. pyogenes comprising administering to said subject an effective amount of the polypeptide encoded by the nucleotide sequence of SEQ ID No. 1.

* * * * *